(12) United States Patent
Hendrix et al.

(10) Patent No.: US 8,741,907 B2
(45) Date of Patent: *Jun. 3, 2014

(54) ALKYL-SUBSTITUTED PYRAZOLOPYRIMIDINES

(75) Inventors: Martin Hendrix, Odenthal (DE); Frank-Gerhard Böβ, Berkshire (GB); Nils Burkhardt, Velbert (DE); Christina Erb, Kriftel (DE); Adrian Tersteegen, Velbert (DE); Marja Van Kampen, Düsseldorf (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 279 days.

This patent is subject to a terminal disclaimer.

(21) Appl. No.: 13/193,931

(22) Filed: Jul. 29, 2011

(65) Prior Publication Data
US 2011/0294834 A1 Dec. 1, 2011

Related U.S. Application Data

(62) Division of application No. 10/524,956, filed as application No. PCT/EP03/08979 on Aug. 13, 2003, now Pat. No. 8,039,477.

(30) Foreign Application Priority Data
Aug. 23, 2002 (DE) .................................. 102 38 724

(51) Int. Cl.
*A61K 31/519* (2006.01)
*A61P 25/28* (2006.01)
*C07D 487/04* (2006.01)

(52) U.S. Cl.
USPC ...................................... 514/262.1; 544/262

(58) Field of Classification Search
USPC ...................................... 544/262; 514/262.1
See application file for complete search history.

(56) References Cited

U.S. PATENT DOCUMENTS

| | | |
|---|---|---|
| 3,165,520 A | 1/1965 | Schmidt et al. |
| 3,169,965 A | 2/1965 | Schmidt et al. |
| 3,211,731 A | 10/1965 | Schmidt et al. |
| 3,732,225 A | 5/1973 | Breuer et al. |
| 5,002,949 A | 3/1991 | Peseckis et al. |
| 5,041,449 A | 8/1991 | Belleau et al. |
| 5,047,407 A | 9/1991 | Belleau et al. |
| 5,053,499 A | 10/1991 | Kojima et al. |
| 5,256,668 A | 10/1993 | Hsu et al. |
| 5,270,315 A | 12/1993 | Belleau |
| 5,294,612 A | 3/1994 | Bacon et al. |
| 5,466,806 A | 11/1995 | Belleau et al. |
| 5,541,187 A | 7/1996 | Bacon et al. |
| 5,563,049 A | 10/1996 | Kojima et al. |
| 5,656,629 A | 8/1997 | Bacon et al. |
| 5,684,164 A | 11/1997 | Belleau et al. |
| 5,750,673 A | 5/1998 | Martin |
| 5,969,116 A | 10/1999 | Martin |
| 5,977,118 A | 11/1999 | Bacon et al. |
| 5,977,332 A | 11/1999 | Martin |
| 6,100,037 A | 8/2000 | Phillips et al. |
| 6,174,884 B1 | 1/2001 | Haning et al. |
| 6,175,008 B1 | 1/2001 | Belleau et al. |
| 6,211,158 B1 | 4/2001 | Seela et al. |
| 6,225,315 B1 | 5/2001 | Ellis |
| 6,350,753 B1 | 2/2002 | Belleau et al. |
| 6,407,114 B1 | 6/2002 | Bunnage et al. |
| 6,458,796 B1 | 10/2002 | Haning et al. |
| 6,479,463 B1 | 11/2002 | Wang et al. |
| 6,831,174 B2 | 12/2004 | Belleau et al. |
| 6,903,224 B2 | 6/2005 | Belleau et al. |
| 7,067,507 B2 | 6/2006 | Pulley et al. |
| 7,122,693 B2 | 10/2006 | Belleau et al. |
| 7,351,827 B2 | 4/2008 | Howell et al. |
| 7,488,733 B2 | 2/2009 | Hendrix et al. |
| 7,615,558 B2 | 11/2009 | Hendrix et al. |
| 7,737,156 B2 | 6/2010 | Boβ et al. |
| 2001/0041797 A1 | 11/2001 | Belleau et al. |

(Continued)

FOREIGN PATENT DOCUMENTS

| | | |
|---|---|---|
| CA | 1 311 201 | 12/1992 |
| CA | 2 283 211 | 9/1998 |

(Continued)

OTHER PUBLICATIONS

Accessed on Mar. 18, 2007, www.mentalhealth.org.uk/information/mental-health-a-z/dementia/.

(Continued)

*Primary Examiner* — Susanna Moore
(74) *Attorney, Agent, or Firm* — Michael P. Morris; Edward S. Lazer

(57) ABSTRACT

The invention relates to alkyl-substituted pyrazolopyrimidines, process for their preparation, and the use thereof for producing medicaments for improving learning and/or memory. The alkyl-substituted pyrazolopyrimidines are of the formula (I):

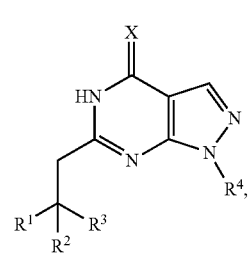

(I)

with the variables as defined in the claims.

7 Claims, No Drawings

(56) References Cited

U.S. PATENT DOCUMENTS

| | | |
|---|---|---|
| 2001/0044441 A1 | 11/2001 | Campbell et al. |
| 2002/0058635 A1 | 5/2002 | Averett |
| 2002/0132754 A1 | 9/2002 | Boss et al. |
| 2003/0087918 A1 | 5/2003 | Belleau et al. |
| 2004/0185459 A1 | 9/2004 | Otsuka et al. |
| 2004/0220186 A1 | 11/2004 | Bell et al. |
| 2004/0254201 A1 | 12/2004 | Belleau et al. |
| 2004/0266736 A1 | 12/2004 | Wunder et al. |
| 2005/0209251 A1 | 9/2005 | Linker et al. |
| 2006/0100222 A1 | 5/2006 | Boss et al. |
| 2006/0106035 A1 | 5/2006 | Hendrix et al. |
| 2006/0111372 A1 | 5/2006 | Hendrix et al. |
| 2006/0111375 A1 | 5/2006 | Shimizu et al. |
| 2006/0258651 A1 | 11/2006 | Linschoten |
| 2007/0037977 A1 | 2/2007 | Belleau et al. |
| 2007/0105876 A1 | 5/2007 | Hendrix et al. |
| 2007/0105881 A1 | 5/2007 | Hendrix et al. |
| 2007/0161662 A1 | 7/2007 | Hendrix et al. |
| 2008/0255118 A1 | 10/2008 | Hendrix et al. |
| 2009/0111838 A1 | 4/2009 | Hendrix et al. |
| 2010/0035900 A1 | 2/2010 | Hendrix et al. |
| 2010/0210839 A1 | 8/2010 | Boess et al. |
| 2011/0015193 A1 | 1/2011 | Eickmeier et al. |
| 2011/0065730 A1 | 3/2011 | Hendrix et al. |
| 2011/0082137 A1 | 4/2011 | Giovannini et al. |

FOREIGN PATENT DOCUMENTS

| | | |
|---|---|---|
| CA | 2 238 211 | 12/1998 |
| CA | 2 357 146 | 7/2000 |
| CA | 2 438 890 | 9/2002 |
| CA | 2 417 631 | 1/2003 |
| CA | 2 484 997 | 4/2003 |
| CA | 2 466 824 | 5/2003 |
| CA | 2 496 194 | 3/2004 |
| CA | 2 496 292 | 4/2004 |
| CA | 2 496 308 | 4/2004 |
| CA | 2 524 900 | 11/2004 |
| CH | 396 923 | 8/1965 |
| CH | 396 924 | 8/1965 |
| CH | 396 925 | 8/1965 |
| CH | 396 927 | 8/1965 |
| CH | 396 926 | 1/1966 |
| CH | 398 626 | 3/1966 |
| DE | 1 147 234 | 4/1963 |
| DE | 1 149 013 | 5/1963 |
| DE | 1 153 023 | 8/1963 |
| DE | 1 156 415 | 10/1963 |
| DE | 2 408 906 | 9/1974 |
| DE | 4 004 558 | 9/1990 |
| DE | 101 56 249 | 5/2003 |
| DE | 102 38 722 | 3/2004 |
| EP | 0 130 735 | 1/1985 |
| EP | 0 286 028 | 10/1988 |
| EP | 496 617 | 7/1992 |
| EP | 0 626 387 | 11/1994 |
| EP | 0 679 657 | 11/1995 |
| EP | 0 995 751 | 4/2000 |
| EP | 1 460 077 | 9/2004 |
| GB | 937 723 | 9/1963 |
| GB | 937 724 | 9/1963 |
| GB | 937 726 | 9/1963 |
| GB | 973 361 | 10/1964 |
| JP | 11 501923 | 2/1999 |
| JP | 2001 514638 | 9/2001 |
| JP | 2002 523507 | 7/2002 |
| JP | 2004 536933 | 12/2004 |
| JP | 2005 531549 | 10/2005 |
| JP | 2006 201272 | 1/2006 |
| JP | 2006 501272 | 1/2006 |
| JP | 2006 503051 | 1/2006 |
| WO | WO-94 14802 | 7/1994 |
| WO | WO-94 17803 | 8/1994 |
| WO | WO-95 10506 | 4/1995 |
| WO | WO-96 28429 | 9/1996 |
| WO | WO-97 16456 | 5/1997 |
| WO | WO-97 46569 | 12/1997 |
| WO | WO-98 00434 | 1/1998 |
| WO | WO-98 10765 | 3/1998 |
| WO | WO-98 16184 | 4/1998 |
| WO | WO-98 40384 | 9/1998 |
| WO | WO-99 41253 | 8/1999 |
| WO | WO-00 18758 | 4/2000 |
| WO | WO-00 43394 | 7/2000 |
| WO | WO-01 05758 | 1/2001 |
| WO | WO-01 60315 | 8/2001 |
| WO | WO-01 77075 | 10/2001 |
| WO | WO-02 06288 | 1/2002 |
| WO | WO-02 09713 | 2/2002 |
| WO | WO-02 16348 | 2/2002 |
| WO | WO-02 055082 | 7/2002 |
| WO | WO-02 057425 | 7/2002 |
| WO | WO-02 068423 | 9/2002 |
| WO | WO-02 074774 | 9/2002 |
| WO | WO-02 086160 | 10/2002 |
| WO | WO-02 098864 | 12/2002 |
| WO | WO-03 011925 | 2/2003 |
| WO | WO-03 022859 | 3/2003 |
| WO | WO-03 037432 | 5/2003 |
| WO | WO-03 037899 | 5/2003 |
| WO | WO-03 041725 | 5/2003 |
| WO | WO-03 072757 | 9/2003 |
| WO | WO-03 093269 | 11/2003 |
| WO | WO-03 099840 | 12/2003 |
| WO | WO-2004 002999 | 1/2004 |
| WO | WO-2004 018474 | 3/2004 |
| WO | WO-2004 026286 | 4/2004 |
| WO | WO-2004 026876 | 4/2004 |
| WO | WO-2004 046331 | 6/2004 |
| WO | WO-2004 096811 | 11/2004 |
| WO | WO-2004 099210 | 11/2004 |
| WO | WO-2004 099211 | 11/2004 |
| WO | WO-2004 108139 | 12/2004 |
| WO | WO-2004 113306 | 12/2004 |
| WO | WO-2005 051944 | 6/2005 |
| WO | WO-2005 068436 | 7/2005 |
| WO | WO-2006 076455 | 7/2006 |
| WO | WO-2006 084281 | 8/2006 |
| WO | WO-2006 091905 | 8/2006 |
| WO | WO-2006 125548 | 11/2006 |
| WO | WO-2007 025043 | 3/2007 |
| WO | WO-2007 046747 | 4/2007 |
| WO | WO-2008 005542 | 1/2008 |
| WO | WO-2008 055959 | 5/2008 |
| WO | WO-2008 100447 | 8/2008 |
| WO | WO-2008 104077 | 9/2008 |
| WO | WO-2008 139293 | 11/2008 |
| WO | WO-2009 068617 | 6/2009 |
| WO | WO-2009 121919 | 10/2009 |
| WO | WO-2010 026214 | 3/2010 |
| WO | WO-2010 112437 | 10/2010 |
| WO | WO-2011 018495 | 2/2011 |

OTHER PUBLICATIONS

Caligiuri, M. et al., "A proteome-wide CDK/CRK—Specific kinase inhibitor promotes tumor cell death in the absence of cell cycle progression," Chemistry & Biology, Oct. 2005, vol. 12, pp. 1103-1115.

Rentero, C. et al., "Identification and distribution of different mRNA variants produced by differential splicing in the human phosphodiesterase 9A gene," Biochemical and Biophysical Research Communications, 2003, vol. 301 pp. 686-692.

Bernabeu, R. et al., "Hippocampal cGMP and cAMP are differentially involved in memory processing of inhibitory avoidance learning," Neuroreport, Jan. 31, 1996, vol. 7, No. 2, pp. 585-588.

Farlow, M. R., "Pharmacokinetic profiles of current therapies for Alzheimer's Disease: Implications for switching to Galantamine," Clinical Therapeutics, 2001, vol. 23, Suppl. A, pp. A13-A24.

Freo, U. et al., "A short review of cognitive and functional neuroimaging studies of cholinergic drugs: implications for therapeutic potentials," Journal of Neural Transmission. 2002, vol. 109, pp. 857-870.

(56) References Cited

OTHER PUBLICATIONS

Intelihealth: "Alzheimer's Disease," Accessed on Jun. 20, 2008, http://www.intelhealth.com/IH/ihtIH/WSIHW000/8303/9117/195703.html?d=dmtHealthAZ.
Intelihealth: "Parkinson's Disease," Accessed on Sep. 22, 2009, http://www.intelihealth,com/IH/ihtIH?d=dmtHealthAZ&c=201957.
Accessed on Dec. 18, 2008, http://en.wikipedia.org/wiki/Amnesia.
Accessed on Dec. 18, 2008, www.mentalhealth.org.uk/information/mental-health-a-z/dementia.
Adreeva, S. G. et al., "Expression of cGMP-Specific Phosphodiesterase 9A mRNA in the Rat Brain", The Journal of Neuroscience, Nov. 15, 2001, vol. 21, No. 22, pp. 9068-9076.
Bagli, J. et al., "Chemistry and Positive Inotropic Effect of Pelrinone and Related Derivatives. A Novel Class of 2-Methylpyrimidones and Inotropic Agents", J. Med. Chem., 1988, vol. 31, pp. 812-823.
Barger et al., "Role of cyclic GMP in the Regulation of Neuronal Calcium and Survival by Secreted Forms of Beta-Amyloid Precursor," J of Neurochem, 1995, vol. 64, No. 5, pp. 2087-2096.
Byrn et al., Solid State Chemistry of Drugs, 1999, vol. 2, No. 10, pp. 232-247.
ChemAbstracts Service, Database Accession No. ALB-H01677136, Database Chemcats, 2007, XP002556399.
Cheng, C. C. et al., "Potential Purine Antagonist VII. Synthesis of 6-Alkylpyrazolo-[3,4-d]pyrimidines$^{12a}$" Potential Purine Antagonists, VII, Feb. 1958, vol. 23, pp. 191-200.
Deninno et al., "The discovery of potent, selective, and orally bioavailable PDE9 inhibitors as potential hypoglycemic agents," Bioorganic & Medicinal Chemistry Letters, 2009, vol. 9, pp. 2537-2541.
Doerwald et al., "Side reactions in organic synthesis," A Guide to Successful Synthesis Design, 2005, 4 pages.
Ebert et al., "Scopolamine model of dementia: electroencephalogram findings and cognitive performance," Europ J of Clinical Investigation, 1998, vol. 28, No. 11, pp. 944-949.
Fawcett, L. et al., "Molecular cloning and characterization of a distance human phosphodiesterase gene family: PDE11A", PNAS, Mar. 28, 2000, vol. 97, No. 7, pp. 3702-3707.
Fisher, D. A. et al., "Isolation and Characterization of PDE8A, a Novel Human cAMP-Specific Phosphodiesterase", Biochemical and Biophysical Research Communications, Apr. 18, 1998, vol. 246, pp. 570-577.
Fisher, D. A. et al., "Isolation and Characterization of PDE9A, a Novel Human cGMP-specific Phosphodiesterase", The Journal of Biological Chemistry, Jun. 19, 1998, vol. 273, No. 25, pp. 15559-15564.
Francais, S. H. et al., "Characterization of a Novel cGMP Binding Protein from Rat Lung", The Journal of Biological Chemistry, Jan. 25, 1980, vol. 255, No. 2, pp. 620-626.
Francis et al., "Cortical Pyramidal Neurone Loss May Cause Glutamaterigic Hypoactivity and Cognitive Impairment in Alzheimer's Disease: Investigative and Therapeutic Perspectives," Journal of Neurochemistry,1993, vol. 60, No. 5, pp. 1589-1604.
Francis et al., "Glutamatergic systems in Alzheimer's disease," International Journal of Geriatric Psychology, 2003, vol. 18, p. S15-S21.
Fujishige, K. et al., "Cloning and Characterization of a Novel Human Phosphodiesterase That Hydrolyzes Both cAMP and cGMP (PDE10A)", The Journal of Biological Chemistry, Jun. 25, 1999, vol. 274, No. 26, pp. 18438-18445.
Gielen, H. et al., "A novel approach to amidines from esters", Tetrahedron Letters, 2002, vol. 43, pp. 419-421.
Gillespie, G. et al., "Characterization of a Bovine Cone Photoreceptor Phosphodiesterase Purified by Cyclic GMP-Sepharose Chromatography", The Journal of Biological Chemistry, Jun. 15, 1988, vol. 263, No. 17, pp. 8133-8141.
Gompper, R. et al., "Substituted dithiocarboxylic acids and ketene thioacteals", Carboxylic Acid Derivatives, 1962, vol. 95, pp. 2861-2870.
Guipponi, M et al., "Identification and characterization of a novel cyclic nucleotide phosphodiesterase gene (PDE9A) that maps to 21q22.3: alternative splicing of mRNA transcripts, genomic structure and sequence", Hum Genet, 1998, vol. 103, pp. 386-392.
Harb et al., "Pyrazoles as building blocks in heterocyclic synthesis..," Chemical Papers, 2005, vol. 59, No. 3, pp. 187-159, XP002498868.
Hendrix et al., "6-cyclymethyl-and 6-alkylmethyl-Substituted Pyrazolopyrimidines," Publication Date: Nov. 18, 2004, Data Supplied from the espacenet database Worldwide; English Abstract of WO 2004099211.
Hendrix et al., "Use of Pyrazolopyrimidine Against Cardiovascular Disease," Publication Date: Nov. 30, 2006, Data Supplied from the espacenet database Worldwide; English Abstract of WO 2006125548.
Hetman, J. M. et al., "Cloning and characterization of PDE7B, a cAMP-specific phosphodiesterase", PNAS, Jan. 4, 2000, vol. 97, No. 1, pp. 472-476.
Huettner, J. E. et al., "Primary Culture of Identified Neurons from the Visual Cortex of Postnatal Rats", The Journal of Neuroscience, 1986, vol. 6, No. 10, pp. 3044-3060.
Hung et al., "A high-yielding synthesis of monalkylhydrazines," Journal of Organic Chemistry, 1981, vol. 46, pp. 5413-5414.
International Preliminary Report on Patentability for PCT/EP2009/061455 dated Mar. 17, 2011.
International Preliminary Report on Patentability for PCT/EP2009/053907 dated Oct. 14, 2010.
International Search Report for International Application No. PCT/EP2004/004455 mailed Sep. 17, 2004, 8 pages.
International Search Report for International Application No. PCT/EP2004/004412 mailed Jul. 14, 2004, 6 pages.
International Search Report for International Application No. PCT/EP03/08979 mailed Nov. 25, 2003, 8 pages.
International Search Report for International Application No. PCT/EP03/08923 mailed Dec. 15, 2003, 6 pages.
International Search Report for International Application No. PCT/EP2004/006477 mailed Oct. 27, 2004, 8 pages.
International Search Report for International Application No. PCT/EP2004/014872 mailed May 19, 2005, 10 pages.
International Search Report for PCT/EP2008/066350 dated Feb. 23, 2009.
International Search Report for PCT/EP2009/053907 dated May 26, 2009.
International Search Report for PCT/EP2009/061455 dated Feb. 19, 2010.
International Search Report for PCT/EP2010/054050 dated May 27, 2010.
International Search Report for PCT/EP2010/061735 dated Sep. 24, 2010.
International Search Report of PCT/EP2003/08880 dated Apr. 16, 2004.
Internet Article, "Dementia", Information from the Mental Health Foundation, Mar. 19, 2008, 3 pages.
Last accessed Jul. 15, 2010http://www.nlm.nih.gov/medlineplus/ency/article/000746.htm.
Loughney, K. et al., "Isolation and Characterization of cDNAs Corresponding to Two Human Calcium, Calmodulin-regulated, 3',5'-Cyclic Nucleotide Phosphodiesterases", The Journal of Biological Chemistry, vol. 271, No. 2, Issue of Jan. 12, 1996, pp. 796-806.
Loughney, K. et al., "Isolation and characterization of cDNAs encoding PDE5A, a human cGMP-binding, cGMP-specific 3',5'-cyclic nucleotide phosphodiesterase", Gene, 1998, vol. 216, pp. 139-147.
Lugnier, C. et al., "Cyclic nucleotide phosphodiesterasse (PDE) superfamily: A new target for the development of specific therapeutic agents", Pharmacology & Therapeutics, 2006, vol. 109, pp. 366-398.
Markwalder, J. A. et al., "Synthesis and Biological Evaluation of 1-Aryl-4,5-dihydro-1 H-pyrazolo[3.4-d]pyrimidin-4-one Inhibitors of Cyclin-Dependent Kinases," J of Med Chemistry, 2004, vol. 47, pp. 5894-5911, XP002399637.
Martins, T. J. et al., "Purification and Characterization of a Cyclic GMP-stimulated Cyclic Nucleotide Phosphoiesterase from Bovine Tissues", The Journal of Biological Chemistry, Feb. 25, 1981, vol. 257, No. 4, pp. 1973-1979.

(56) References Cited

OTHER PUBLICATIONS

Miki, T. et al., "Characterization of the cDNA and Gene Encoding Human PDE3B, the cGIP1 Isoform of the Human Cyclic GMP-Inhibited Cyclic Nucleotide Phosphodiesterase Family", Genomics, 1996, vol. 36, pp. 476-485.

Miyashita, A. et al., "Studies on Pyrazolo[3,4-d]Pyrimidine Derivatives", Heterocycle, 1990, vol. 31, No. 7, pp. 1309-1314.

Murashima, S. et al., "Characterization of Particulate Cyclic Nucleotide Phosphodiesterases from Bovine Brain: Purification of a Distinct cGMP-Stimulated lsognzyme," Biochemistry, 1990, vol. 29, pp. 5285-5292.

Obernotle, R. et al., "The cDNA of a human lymphocyte cyclic-AMP phosphodiesterase (PDE IV) reveals a multigene family", Gene, 1993, vol. 29, pp. 239-247.

Podraza et al., "Reductive Cyclization of Ketoesters Utilizing Sodium Cyanoborohydride: Synthesis of γ- and σ-lactones," J of Heterocyclic Chem., 1987, vol. 24, pp. 293.

Prickaerts et al., "Effects of two selective phosphodiesterase type 5 inhibitors, sildenafil and vardenafil, on object recognition memory and hippocampal cyclic gmp levels in the rat," Neuroscience, 2002, vol. 113, pp. 351-361.

Prickaerts et al., "Possible role of nitric oxide-cyclic GMP pathway in object recognition memory: Effects of 7 nitroindazole and zaprinast," Europ J of Pharmacology, 1997, vol. 337, No. 2-3, pp. 125-136.

Puzzo et al., "Amyloid-Beta Peptide Inhibits Activation of the Nitric Oxide/Cgmp/Camp-Responsive Element-Binding Protein Pathway during Hippocampal Synaptic Plasticity," The Journal of Neuroscience, 2005, vol. 25, No. 29, pp. 6887-6897.

Reddy, K. H. et al., "Versatile synthesis of 6-alkyl/aryl-1H-pyrazolo[3,4-d]pyrimidin-4[5H]-ones", Indian Journal of Chemistry, Mar. 1992, vol. 31 B, pp. 163-166.

Reid et al., "Role of Phosphodiesterase isoenzymes in the control of renin secretion: effects of selective enzyme inhibitors," Current Pharmaceutical Design, 1999, vol. 5, No. 9, pp. 725-735.

Related U.S. Appl. No. 12/855,129, filed Aug. 12, 2010.
Related U.S. Appl. No. 12/935,686, filed Sep. 30, 2010.
Related U.S. Appl. No. 13/062,625, filed Mar. 7, 2011.
Related U.S. Appl. No. 13/099,064, filed May 2, 2011.

Reymann et al., "The late maintenance of hippocampal LTP: Requirements, phases, 'synaptic tagging', 'late-associativity' and implications," Neuropharmacology, 2007, vol. 52, pp. 24-40.

Roenn, M. et al., "Palladium (II)-Catalyzed Cyclization Using Molecular Oxygen as Reoxidant", Tetrahedron Letters, 1995, vol. 36, No. 42, pp. 7749-7752.

Rosman, G. J. et al., "Isolation and Characterization of human cDNAs encoding a cGMP-stimulated 3',5'-cyclic nucleotide phosphodiesterase", Gene, 1997, vol. 191, pp. 89-95.

Schmidt et al., "Pyrazolo[3, 4-d] pyrimidin-nucleoside," Chemische Berichte, 1977, vol. 110, pp. 2445-2455.

Schmidt, P. et al., "A new synthesis of pyrazolo [3,4-d] pyrimidines having coronary dilation properties", Helvetica Chimica Acta, 1962, vol. XLV, fascicule V, No. 189, pp. 1620-1627.

Schousboe, A. et al., "Role of $CA^{++}$ and Other Second Messengers in Excitatory Amino Acid Receptor Mediated Neurodegeneration: Clinical Perspectives", Clinical Neuroscience, 1997, vol. 4, pp. 194-198.

Skipper et al., "Structure-Activity Relationships Observed on Screening a Series of Pyrazolopyrimidines against Experimental Neoplasms," Cancer Research, 1957, vol. 17, pp. 579-596.

Soderling, S. H. et al., "Identification and Characterization of a Novel Family of Cyclic Nucleotide Phosphodiesterases", The Journal of Biological Chemistry, Jun. 19, 1998, vol. 273, No. 25, pp. 15553-15558.

Soderling, S. H. et al., "Regulation of cAMP and cGMP signaling: new phosphodiesterases and new functions", Current Opinion in Cell Biology, 2000, vol. 12, pp. 174-179.

Timberlake et al., "Chemistry of Hydrazo-, Azo-, and Azoxy Groups," Patai, 1975, Chapter 4.

Ugarkar et al., "Synthesis and antiviral/antitumor activities of . . . ," Journal of Medicinal Chemistry, 1984, vol. 27, No. 8, pp. 1026-1030.

Ulrich, J. et al., "Crystallization", Kirk-Othmer Encyclopedia of Chemical Technology, Aug. 16, 2002, 7 pages.

Van Der Staay, J. et al., "The novel selective PDE9 inhibitor Bay 73-6691 improves learning and memory in rodents", Neuropharmacology, 2008, vol. 55, pp. 908-916.

Van Staveren et al., Journal of Neurocytology, 2002, vol. 31, pp. 729-741.

Vippagunta, S. R. et al., "Crystalline Solids", Advanced Drug Delivery Reviews, 2001, vol. 48, pp. 3-26.

Wang et al., "Identification and characterization of a new human type 9 cGMP-specific phosphodiesterase-splice variant (PDE9A5) Different tissue distribution and subcellular localization of PDE9A variants," Gene, 2003, vol. 314, pp. 15-27.

Wang et al., "Insight into binding of phosphodiesterase-9-A selective inhibitors by crystal structures and mutagenesis," J. Med. Chem., Oct. 12, 2009.

Weeber, E. J. et al., "Molecular Genetics of Human Cognition", Molecular Inventions, Oct. 2002, vol. 2, No. 6, pp. 376-391.

Wei, J. et al., "Molecular and Pharmacological Analysis of Cyclic Nucleotide-Gated Channel Function in the Central Nervous System", Progress in Nueorobiology, 1998, vol. 56, pp. 37-64.

West, A. R. et al., "Solid Solutions", Department of Chemistry University of Aberdeen, Mar. 3, 1988, 3 pages.

Wunder, F. et al., "Characterization of the First Potent and Selective PDE9 Inhibitor Using a cGMP Reporter Cell Line," Molecular Pharmacology, 2005, vol. 68, No. 6, pp. 1775-1781.

Hale et al. "1,3,4-Trisubstituted Pyrrolidine CCR5 Receptor Antagonists. Part 3: Polar Functionality and Its Effect on Anti-HIV-1 Activity", Bioorganic & Medicinal Chemistry Letters, 12:2997-3000, (2002).

Sundelin et al. "Synthesis and Biological Activity of Some Carbocyclic Analogs of Muscarine", Journal of Medicinal Chemistry,16(3):235-239, (1973).

ALKYL-SUBSTITUTED PYRAZOLOPYRIMIDINES

This application is a divisional of U.S. Ser. No. 10/524,956, filed Dec. 15, 2005 now U.S. Pat. No. 8,039,477; U.S. Ser. No. 10/524,956 is a 371 National stage application of PCT/EP2003/008979 filed Aug. 13, 2003.

The invention relates to novel alkyl-substituted pyrazolopyrimidines, process for their preparation, and the use thereof for producing medicaments for improving perception, concentration, learning and/or memory.

The cellular activation of adenylate cyclases and guanylate cyclases effects cyclization respectively of ATP and GTP to 5'-3'cyclic adenosine monophosphate (cAMP) and 5'-3'cyclic guanosine monophosphate (cGMP). These cyclic nucleotides (cAMP and cGMP) are important second messengers and therefore play a central role in cellular signal transduction cascades. Each of them reactivates inter alia, but not exclusively, protein kinases. The protein kinase activated by cAMP is called protein kinase A (PKA), and the protein kinase activated by cGMP is called protein kinase G (PKG). Activated PKA and PKG are able in turn to phosphorylate a number of cellular effector proteins (e.g. ion channels, G-protein-coupled receptors, structural-proteins). It is possible in this way for the second messengers cAMP and cGMP to control a wide variety of physiological processes in a wide variety of organs. However, the cyclic nucleotides are also able to act directly on effector molecules. Thus, it is known, for example, that cGMP is able to act directly on ion channels and thus is able to influence the cellular ion concentration (review in: Wei et al., *Prog. Neurobiol.*, 1998, 56: 37-64). The phosphodiesterases (PDE) are a control-mechanism for controlling the activity of cAMP and cGMP and thus in turn these physiological processes. PDEs hydrolyze the cyclic monophosphates to the inactive monophosphates AMP and GMP. At least 21 PDE genes have now been described (*Exp. Opin. Investig. Drugs* 2000, 9, 1354-3784). These 21 PDE genes can be divided on the basis of their sequence homology into 11 PDE families (for proposed nomenclature, see http://depts.washington.edu/pde/Nomenclature.html.). Individual PDE genes within a family are differentiated by letters (e.g. PDE1A and PDE1B). If different splice variants within a gene also occur, this is then indicated by an additional numbering after the letters (e.g. PDE1A1).

Human PDE9A was cloned and sequenced in 1998. The amino acid identity with other PDEs does not exceed 34% (PDE8A) and is never less than 28% (PDE5A). With a Michaelis-Menten constant (Km) of 170 nM, PDE9A has high affinity for cGMP. In addition, PDE9A is selective for cGMP (Km for cAMP=230 µM). PDE9A has no cGMP binding domain, suggesting allosteric enzyme regulation by cGMP. It was shown in a Western blot analysis that PDE9A is expressed in humans inter alia in testes, brain, small intestine, skeletal muscle, heart, lung, thymus and spleen. The highest expression was found in the brain, small intestine, heart and spleen (Fisher et al., *J. Biol. Chem.*, 1998, 273 (25): 15559-15564). The gene for human PDE9A is located on chromosome 21q22.3 and comprises 21 exons. To date, 4 alternative splice variants of PDE9A have been identified (Guipponi et al, *Hum. Genet.*, 1998, 103: 386-392). Classical PDE inhibitors do not inhibit human PDE9A. Thus, IBMX, dipyridamole, SKF94120, rolipram and vinpocetine show no inhibition on the isolated enzyme in concentrations of up to 100 µM. An $IC_{50}$ of 35 µM has been demonstrated for zaprinast (Fisher et al., *J. Biol. Chem.*, 1998, 273 (25): 15559-15564).

Murine PDE9A was cloned and sequenced in 1998 by Soderling et al. (*J. Biol. Chem.*, 1998, 273 (19): 15553-15558). This has, like the human form, high affinity for cGMP with a Km of 70 nM. Particularly high expression was found in the mouse kidney, brain, lung and heart. Murine PDE9A is not inhibited by IBMX in concentrations below 200 µM either; the $IC_{50}$ for zaprinast is 29 µM (Soderling et al., *J. Biol. Chem.*, 1998, 273 (19): 15553-15558). It has been found that PDE9A is strongly expressed in some regions of the rat brain. These include olfactory bulb, hippocampus, cortex, basal ganglia and basal forebrain (Andreeva et al., *J. Neurosci.*, 2001, 21 (22): 9068-9076). The hippocampus, cortex and basal forebrain in particular play an important role in learning and memory processes.

As already mentioned above, PDE9A is distinguished by having particularly high affinity for cGMP, PDE9A is therefore active even at low physiological concentrations, in contrast to PDE2A (Km=10 µM; Martins et al., *J. Biol. Chem.*, 1982, 257: 1973-1979), PDE5A (Km=4 µM; Francis et al., *J. Biol. Chem.*, 1980, 255: 620-626), PDE6A (Km=17 µM; Gillespie and Beavo, *J. Biol. Chem.*, 1988, 263 (17): 8133-8141) and PDE11A (Km=0.52 µM; Fawcett et al., *Proc. Nat. Aced. Sci.*, 2000, 97 (7): 3702-3707). In contrast to PDE2A (Murashima et al., *Biochemistry*, 1990, 29: 5285-5292), the catalytic activity of PDE9A is not increased by cGMP because it has no GAF domain (cGMP-binding domain via which the PDE activity is allosterically increased) (Beavo et al., *Current Opinion in Cell Biology*, 2000, 12: 174-179). PDE9A inhibitors may therefore lead to an increase in the baseline cGMP concentration. This increase in the baseline cGMP concentration surprisingly leads to an improvement in learning and memory in the social recognition test.

WO 98/40384 discloses pyrazolopyrimidines which are PDE1, 2 and 5 inhibitors and can be employed for the treatment of cardiovascular and cerebrovascular disorders and disorders of the urogenital system.

CH 396 924, CH 396 925, CH 396 926, CH 396 927, DE 1 147 234, DE 1 149 013, GB 937,726 describe pyrazolopyrimidines which have a coronary-dilating effect and which can be employed for the treatment of disturbances of myocardial blood flow.

U.S. Pat. No. 3,732,225 describes pyrazolopyrimidines which have an antiinflammatory and blood glucose-lowering effect.

DE 2 408 906 describes styrenepyrazoloprimidines which can be employed as antimicrobial and antiinflammatory agents for the treatment of, for example, edema.

The present invention relates to compounds of the formula

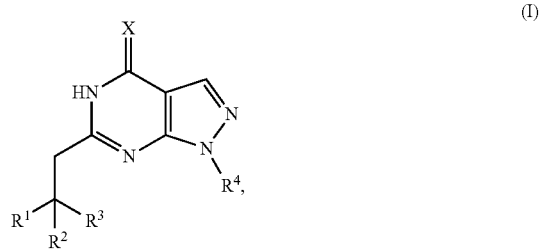

(I)

in which

R$^1$ is $C_1$-$C_6$-alkyl, trifluoromethyl, hydroxy, $C_1$-$C_6$-alkoxy, —C(=O)OR$^5$ or —C(=O)NR$^6$R$^7$, where $C_1$-$C_6$-Alkyl is optionally substituted by 1 to 3 radicals independently of one another selected from the group of hydroxy, $C_1$-$C_6$-alkoxy, halogen, trifluoromethyl, trifluoromethoxy, —C(=O)OR$^5$ or —C(=O)NR$^6$R$^7$, and R$^5$ is $C_1$-$C_6$-alkyl, $R^6$ and $R^7$ are independently of one another hydrogen, $C_6$-$C_{10}$-aryl, $C_1$-$C_6$-alkyl, or
together with the nitrogen atom to which they are bonded form a 4- to 10-membered heterocyclyl,
$R^2$ is hydrogen, $C_1$-$C_6$-alkyl, trifluoromethyl, $C_1$-$C_6$-alkoxy, or
$R^1$ and $R^2$ together with the carbon atom to which they are bonded form $C_3$-$C_8$-cycloalkyl, $C_3$-$C_8$-cycloalkenyl or 4- to 10-membered heterocyclyl, which are optionally substituted by up to 2 substituents from the group of $C_1$-$C_6$-alkyl, $C_1$-$C_6$-alkoxy, hydroxy, oxo, —C(=O)OR$^8$, and
$R^8$ is $C_1$-$C_6$-alkyl or benzyl,
$R^3$ is hydrogen or $C_1$-$C_6$-alkyl,
$R^4$ is pentan-3-yl, $C_3$-$C_6$-cycloalkyl,
X is oxygen or sulfur, the salts, solvates and/or solvates of the salts thereof.

Compounds of the invention are the compounds of the formula (I) and the salts, solvates and solvates of the salts thereof; the compounds which are encompassed by formula (I) and have the formulae mentioned hereinafter and the salts, solvates and solvates of the salts thereof, and the compounds which are encompassed by formula (I) and are mentioned hereinafter as exemplary embodiments and the salts, solvates and solvates of the salts thereof, where the compounds which are encompassed by formula (I) and are mentioned hereinafter are not already salts, solvates and solvates of the salts.

The compounds of the invention may, depending on their structure, exist in stereoisomeric forms (enantiomers, diastereomers). The invention therefore relates to the enantiomers or diastereomers and respective mixtures thereof. The sterically pure constituents can be isolated in a known manner from such mixtures of enantiomers and/or diastereomers.

Salts which are preferred for the purposes of the invention are physiologically acceptable salts of the compounds of the invention.

Physiologically acceptable salts of the compounds (I) include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Physiologically acceptable salts of the compounds (I) also include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dehydroabietylamine, arginine, lysine, ethylenediamine and methylpiperidine.

Solvates refers for the purposes of the invention to those forms of the compounds which form, in the solid or liquid state, a complex by coordination with solvent-molecules. Hydrates are a specific form of solvates in which the coordination takes place with water.

In addition, the present invention also encompasses prodrugs of the compounds of the invention. The term "prodrugs" encompasses compounds which themselves may be biologically active or inactive but are converted (for example by metabolism or hydrolysis) into compounds of the invention during their residence time in the body.

For the purposes of the present invention, the substituents have the following meaning, unless specified otherwise:

$C_1$-$C_6$-Alkoxy is a straight-chain or branched alkoxy radical having 1 to 6, preferably 1 to 4, particularly preferably having 1 to 3 carbon atoms. Nonlimiting examples include methoxy, ethoxy, n-propoxy, isopropoxy, tert-butoxy, n-pentoxy and n-hexoxy.

$C_1$-$C_6$-Alkyl is a straight-chain or branched alkyl radical having 1 to 6, preferably 1 to 4, particularly preferably 1 to 3, carbon atoms. Nonlimiting examples include methyl, ethyl, n-propyl, isopropyl, tert-butyl, n-pentyl and n-hexyl.

$C_6$-$C_{10}$-Aryl is phenyl or naphthyl.

$C_3$-$C_8$-Cycloalkyl is cyclopropyl, cyclopentyl, cyclobutyl, cyclohexyl, cycloheptyl or cyclooctyl. Cyclopropyl, cyclopentyl and cyclohexyl may be mentioned as preferred.

$C_3$-$C_8$-Cycloalkenyl is partially unsaturated, nonaromatic cycloalkyl radicals which comprise one or more multiple bonds, preferably double bonds. Nonlimiting examples include cyclopentenyl, cyclohexenyl and cycloheptenyl.

Halogen is fluorine, chlorine, bromine and iodine. Fluorine, chlorine, bromine are preferred, and fluorine and chlorine are particularly preferred.

4- to 10-membered heterocyclyl is a mono- or polycyclic, heterocyclic radical having 4 to 10 ring atoms and up to 3, preferably 1, heteroatoms or hetero groups from the series N, O, S, SO, $SO_2$. 4- to 8-membered heterocyclyl is preferred. Mono- or bicyclic heterocyclyl is preferred. N and O are preferred as heteroatoms. The heterocyclyl radicals may be saturated or partially unsaturated. Saturated heterocyclyl radicals are preferred. The heterocyclyl radicals may be bonded via a carbon atom or a heteroatom. 5- to 7-membered, monocyclic saturated heterocyclyl radicals having up to two heteroatoms from the series O, N and S are particularly preferred. Preferred examples which may be mentioned are: oxetan-3-yl, pyrrolidin-2-yl, pyrrolidin-3-yl, pyrrolinyl, tetrahydrofuranyl, tetrahydrothienyl, pyranyl, piperidinyl, thiopyranyl, morpholinyl, perhydroazepinyl.

When radicals in the compounds of the invention are optionally substituted, unless otherwise specified, substitution by up to three identical or different substituents is preferred.

The compounds of the invention may also be in the form of tautomers, shown by way of example below:

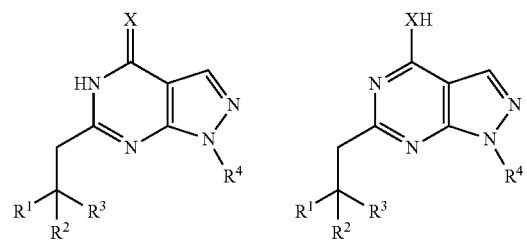

A further embodiment of the invention relates to compounds of the formula (I), where
$R^1$ is $C_1$-$C_6$-alkyl, hydroxy, $C_1$-$C_6$-alkoxy, —C(=O)OR$^5$ or —C(=O)NR$^6$R$^7$, where $C_1$-$C_6$-alkyl is optionally substituted by hydroxy, $C_1$-$C_6$-alkoxy, —C(=O)OR$^5$ or —C(=O)NR$^6$R$^7$, and
$R^5$ is $C_1$-$C_6$-alkyl,
$R^6$ and $R^7$ are independently of one another hydrogen, $C_6$-$C_{10}$-aryl, $C_1$-$C_6$-alkyl, or
together with the nitrogen atom to which they are bonded form a 4- to 10-membered heterocyclyl, $R^2$ is hydrogen, $C_1$-$C_6$-alkyl, $C_3$-$C_6$-alkoxy,
or
$R^1$ and $R^2$ together with the carbon atom to which they are bonded form $C_3$-$C_8$-cycloalkyl, $C_3$-$C_8$-cycloalkenyl or 4- to 10-membered heterocyclyl, which are optionally substituted by up to 2 substituents from the group of $C_1$-$C_6$-alkyl, $C_1$-$C_6$-alkoxy, hydroxy, oxo, —C(=O)OR$^8$, and
$R^8$ is $C_1$-$C_6$-alkyl or benzyl,
$R^3$ is hydrogen or $C_1$-$C_6$-alkyl,
$R^4$ is pentan-3-yl, $C_4$-$C_6$-cycloalkyl,
X is oxygen or sulfur, the salts, solvates and/or solvates of the salts thereof.

A further embodiment of the invention relates to compounds of the formula (I), where
$R^1$ is $C_1$-$C_4$-alkyl, trifluoromethyl, hydroxy, $C_1$-$C_4$-alkoxy, —C(=O)OR$^5$ or —C(=O)NR$^6$R$^7$, where $C_1$-$C_4$-alkyl is optionally substituted by hydroxy, $C_1$-$C_4$-alkoxy, trifluoromethyl, —C(=O)OR$^5$ or —C(=O)NR$^6$R$^7$, and
$R^5$ is $C_1$-$C_4$-alkyl,
$R^6$ and $R^7$ are independently of one another hydrogen, phenyl, $C_1$-$C_4$-alkyl, or
together with the nitrogen atom to which they are bonded form a 5- to 6-membered heterocyclyl,
$R^2$ is hydrogen, $C_1$-$C_4$-alkyl, $C_1$-$C_4$-alkoxy, trifluoromethyl,
or
$R^1$ and $R^2$ together with the carbon atom to which they are bonded form $C_5$-$C_6$-cycloalkyl, $C_5$-$C_6$-cycloalkenyl or 5- to 6-membered heterocyclyl, which are optionally substituted by up to 2 substituents from the group of $C_1$-$C_4$-alkyl, $C_1$-$C_4$-alkoxy, hydroxy, oxo, —C(=O)OR$^8$, and
$R^8$ is $C_1$-$C_4$-alkyl or benzyl,
$R^3$ is hydrogen,
$R^4$ is pentan-3-yl, $C_5$-$C_6$-cycloalkyl,
X is oxygen or sulfur, the salts, solvates and/or solvates of the salts thereof.

A further embodiment of the invention relates to compounds of the formula (I), where
$R^1$ is methyl, ethyl, isopropyl, trifluoromethyl, methoxycarbonyl, ethoxycarbonyl or —C(=O)NR$^6$R$^7$, where methyl is optionally substituted by methoxycarbonyl or ethoxycarbonyl, and
$R^6$ is phenyl, and
$R^7$ is hydrogen,
$R^2$ is hydrogen, methyl, trifluoromethyl, or
$R^1$ and $R^2$ together with the carbon atom to which they are bonded form cyclopentyl, cyclohexyl, cyclopentenyl or tetrahydrofuryl, where cyclohexyl is optionally substituted by methyl, and
$R^3$ is hydrogen,
$R^4$ is pentan-3-yl, $C_5$-$C_6$-cycloalkyl,
X is oxygen or sulfur, the salts or solvates and/or solvates of the salts thereof.

A further embodiment of the invention relates to compounds of the formula (I), where
$R^1$ is methyl, ethyl, isopropyl, methoxycarbonyl, ethoxycarbonyl or —C(=O)NR$^6$R$^7$, where methyl is optionally substituted by methoxycarbonyl or ethoxycarbonyl, and
$R^6$ is phenyl, and
$R^7$ is hydrogen,
$R^2$ is hydrogen, methyl, or
$R^1$ and $R^2$ together with the carbon atom to which they are bonded form cyclopentyl, cyclohexyl, cyclopentenyl or tetrahydrofuryl, where cyclohexyl is optionally substituted by methyl, and
$R^3$ is hydrogen,
$R^4$ is pentan-3-yl, $C_5$-$C_6$-cycloalkyl, X is oxygen, the salts, solvates and/or solvates of the salts thereof.

A process for preparing the compounds of the invention of the formula (I) has additionally been found, characterized in that either
[A] compounds of the formula

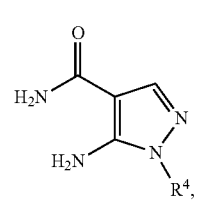

(II)

in which $R^4$ has the meanings indicated above,
are converted by reaction with a compound of the formula

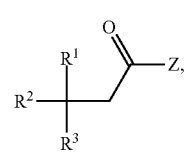

(IIIa)

in which $R^1$, $R^2$ and $R^3$ have the meanings indicated above, and
Z is chlorine or bromine,
in an inert solvent and in the presence of a base initially into compounds of the formula

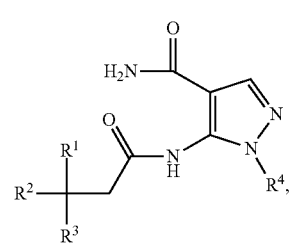

(IV)

in which $R^1$, $R^2$, $R^3$ and $R^4$ have the meanings indicated above,
then cyclized in an inert solvent in the presence of a base to compounds of the formula

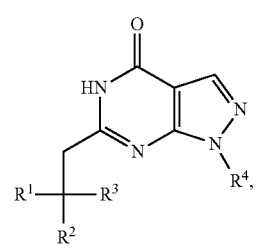

(IA)

in which $R^1$, $R^2$, $R^3$ and $R^4$ have the meanings indicated above, or

[B] compounds of the formula (II) are reacted, with direct cyclization to (IA), with a compound of the formula

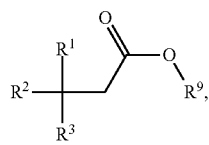

(IIIb)

in which $R^1$, $R^2$ and $R^3$ have the meanings indicated above, and $R^9$ is methyl or ethyl, in an inert solvent and in the presence of a base, or

[C] compounds of the formula

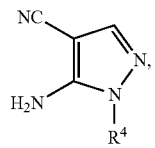

(V)

in which $R^4$ has the meanings indicated above, are initially converted by reaction with a compound of the formula (IIIa) in an inert solvent and in the presence of a base into compounds of the formula

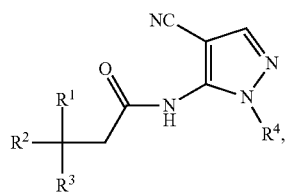

(VI)

in which $R^1$, $R^2$, $R^3$ and $R^4$ have the meanings indicated above, and the latter are cyclized in a second step in an inert solvent and in the presence of a base and of an oxidizing agent to (IA), the compounds of the formula (IA) are where appropriate then converted by reaction with a sulfurizing agent such as, for example, diphosphorus pentasulfide into the thiono derivatives of The formula

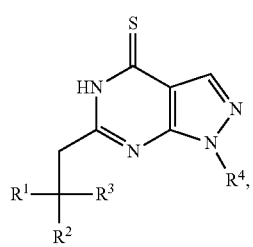

(IB)

in which $R^1$, $R^2$, $R^3$ and $R^4$ have the meanings indicated above, the resulting compounds of the formula (I) are reacted where appropriate with the appropriate (i) solvents and/or (ii) bases or acids to give the solvates, salts and/or solvates of the salts thereof.

Suitable for the first step of process [A] and process [C] are inert organic solvents which are not changed under the reaction conditions. These preferably include ethers such as, for example, diethyl ether, dioxane, tetrahydrofuran or glycol dimethyl ether, or toluene or pyridine. It is likewise possible to employ mixtures of the solvents mentioned. Tetrahydrofuran, toluene or pyridine are particularly preferred.

Bases suitable in general are alkali metal hydrides such as, for example, sodium hydride, or cyclic amines such as, for example, piperidine, pyridine, dimethylaminopyridine (DMAP), or $C_1$-$C_4$-alkylamines such as, for example, triethylamine. Sodium hydride, pyridine and/or dimethylaminopyridine are preferred.

The base is generally employed in an amount of from 1 mol to 4 mol, preferably from 1.2 mol to 3 mol, in each case based on 1 mol of the compounds of the general formula (II) or (V).

In one variant, the reaction is carried out in pyridine, to which a catalytic amount of DMAP is added. It is also possible where appropriate to add toluene.

The reaction temperature can generally be varied within a relatively wide range. The range is generally from −20° C. to +200° C., preferably from 0° C. to +100° C.

Solvents for the cyclization in the second step of processes [A] and [C] are the usual organic solvents. These preferably include alcohols such as methanol, ethanol, propanol, isopropanol, n-butanol or tert-butanol, or ethers such as tetrahydrofuran or dioxane, or dimethylformamide or dimethyl sulfoxide. Alcohols such as methanol, ethanol, propanol, isopropanol or tert-butanol are particularly preferably used. It is likewise possible to employ mixtures of the solvents mentioned.

Bases suitable for the cyclization in the second step of processes [A] and [C] are the usual inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate or sodium bicarbonate or alkali metal alcoholates such as sodium methanolate, sodium ethanolate, potassium methanolate, potassium ethanolate or potassium tert-butanolate. Potassium carbonate, sodium hydroxide and potassium tert-butanolate are particularly preferred.

When carrying out the cyclization, the base is generally employed in an amount of from 2 mol to 6 mol, preferably from 3 mol to 5 mol, in each case based on 1 mol of the compounds of the general formula (IV) or (VI).

Oxidizing agents suitable for the cyclization in the second step of process [C] are, for example, hydrogen peroxide or sodium borate. Hydrogen peroxide is preferred.

The cyclization in processes [A], [B] and [C] is generally carried out in a temperature range from 0° C. to +160° C., preferably at the boiling point of the particular solvent.

The cyclization is generally carried out under atmospheric pressure. However, it is also possible to carry out the process under elevated pressure or under reduced pressure (e.g. in a range from 0.5 to 5 bar).

Solvents suitable for process [B] are the alcohols mentioned above for the second step of processes [A] and [C], with preference for ethanol.

Bases suitable for process [B] are alkali metal hydrides such as, for example, sodium or potassium hydride, or alkali metal alcoholates such as, for example, sodium methanolate, ethanolate, isopropoxide or potassium tert-butoxide. Sodium hydride is preferred.

The base is employed in an amount of from 2 mol to 8 mol, preferably from 3 mol to 6 mol, in each case based on 1 mol of the compounds of the formula (II).

The compounds of the formula (II) are known or can be prepared for example by initially condensing ethoxymethyl-enemalononitrile with hydrazine derivatives of the formula (VII)

in which $R^4$ has the meanings indicated above,
in an inert solvent to give the pyrazole nitriles of the formula (V), and then reacting the latter with one of the oxidizing agents mentioned above, preferably hydrogen peroxide, in the presence of ammonia [cf., for example, A. Miyashita et al., Heterocycles 1990, 31, 1309ff].

The compounds of the formulae (IIIa), (IIIb) and (VII) are commercially available, known from the literature or can be prepared in analogy to processes known from the literature.

The process of the invention can be illustrated by way of example by the following formula diagram:

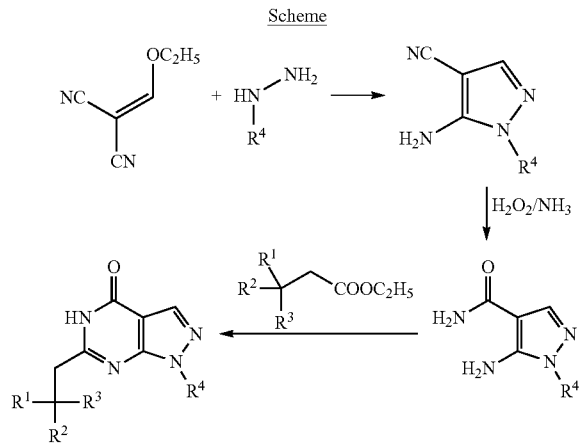

Compounds of the formula (IA) and (IB) can be further modified where appropriate within the scope of the meanings of $R^1$, $R^2$, and $R^3$ by standard processes.

Further processes for preparing pyrazolo[3,4-d]pyrimidin-4-ones are known and can likewise be employed to synthesize the compounds of the invention (see, for example: P. Schmidt et al., Helvetica Chimica Acta 1962, 189, 1620ff.).

The compounds of the invention show a valuable range of pharmacological and pharmacokinetic effects which could not have been predicted.

They are therefore suitable for use as medicaments for the treatment and/or prophylaxis of diseases in humans and animals.

The term "treatment" for the purposes of the present invention includes prophylaxis.

It has surprisingly been found that selective PDE9A inhibitors are suitable for producing medicaments for improving perception, concentration, learning or memory.

The compounds of the invention can, by reason of their pharmacological properties, be employed alone or in combination with other medicaments for improving perception, concentration, learning and/or memory.

The present invention further relates to a method for the treatment and/or prophylaxis of disorders, in particular the aforementioned disorders, using an effective amount of the compounds of the invention.

A PDE9A inhibitor for the purposes of the invention is a compound which inhibits human PDE9A under the conditions indicated below with an $IC_{50}$ of less than 10 µM, preferably less than 1 µM.

A selective PDE9A inhibitor for the purposes of the invention is a compound which inhibits human PDE9A under the conditions indicated below more strongly than human PDE1C, PDE2A, PDE3B, PDE4B, PDE5A, PDE7B, PDE8A, PDE10A and PDE11. An $IC_{50}$ (PDE9A)/$IC_{50}$ (PDE1C, PDE2A, PDE3B, PDE4B, PDE5A, PDE7B and PDE10A) ratio of less than 0.2 is preferred.

The selective PDE9A inhibitors are particularly suitable for improving perception, concentration, learning or memory after cognitive impairments like those occurring in particular in situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotrophic lateral sclerosis (ALS), Huntington's disease, multiple sclerosis, thalamic degeneration, Creutzfeld-Jacob dementia, HIV dementia, schizophrenia with dementia or Korsakoff's psychosis.

The in vitro effect of the compounds of the invention can be shown with the following biological assays:

PDE Inhibition

Recombinant PDE1C (GenBank/EMBL Accession Number: NM_005020, Loughney et al. *J. Biol. Chem.* 1996 271, 796-806), PDE2A (GenBank/EMBL Accession Number: NM_002599, Rosman et al. *Gene* 1997 191, 89-95), PDE3B (GenBank/EMBL Accession Number: NM_000922, Miki et al. *Genomics* 1996, 36, 476-485), PDE4B (GenBank/EMBL Accession Number: NM_002600, Obernolte et al. *Gene.* 1993, 129, 239-247), PDE5A (GenBank/EMBL Accession Number: NM_001083, Loughney et al. *Gene* 1998, 216, 139-147), PDE7B (GenBank/EMBL Accession Number: NM_018945, Hetman et al. *Proc. Natl. Acad. Sci. U.S.A.* 2000, 97, 472-476), PDE8A (GenBank/EMBL Accession Number. AF_056490, Fisher et al. *Biochem. Biophys. Res. Commun.* 1998 246, 570-577), PDE9A (Fisher et al., J. Biol. Chem, 1998, 273 (25): 15559-15564), PDE10A (GenBank/EMBL Accession Number: NM_06661, Fujishige et al. *J Biol Chem.* 1999, 274, 18438-45), PDE11A (GenBank/EMBL Accession Number: NM_016953, Fawcett et al. *Proc. Natl. Acad. Sci.* 2000, 97, 3702-3707) were expressed in Sf9 cells with the aid of the pFASTBAC bacialovirus expression system (GibcoBRL).

The test substances are dissolved in 100% DMSO and serially diluted to determine their in vitro effect on PDE 9A. Typically, serial dilutions from 200 µM to 1.6 µM are prepared (resulting final concentrations in the assay: 4 µM to 0.032 µM). 2 µL portions of the diluted substance solutions are introduced into the wells of microtiter plates (Isoplate; Wallac Inc., Atlanta, Ga.). Then 50 µL of a dilution of the PDE9A preparation described above are added. The dilution of the PDE9A preparation is chosen so that less than 70% of the substrate is converted during the subsequent incubation (typical dilution: 1:10000; dilution buffer: 50 mM Tris/HCl pH 7.5, 8.3 mM $MgCl_2$, 1.7 mM EDTA, 0.2% BSA). The substrate, [8-$^3$H] guanosine 3',5'-cyclic phosphate (1 µCi/µL; Amersham Pharmacia Biotech., Piscataway, N.J.) is diluted 1:2000 with assay buffer (50 mM Tris/HCl pH 7.5, 8.3 mM MgCl$_2$, 1.7 mM EDTA) to a concentration of 0.0005 μCi/μL. The enzyme reaction is finally started by adding 50 μL (0.025 μCi) of the diluted substrate. The assay mixtures are incubated at room temperature for 60 min and the reaction is stopped by adding 25 μl of a PDE9A inhibitor (e.g. the inhibitor from preparation example 1, final concentration 10 μM) dissolved in assay buffer. Immediately thereafter, 25 μL of a suspension containing 18 mg/mL Yttrium Scintillation Proximity Beads (Amersham Pharmacia Biotech., Piscataway, N.J.) are added. The microliter plates are sealed with a film and left to stand at room temperature for 60 min. The plates are then measured for 30 s per well in a Microbeta scintillation counter (Wallac Inc., Atlanta, Ga.). IC$_{50}$ values are determined from the graphical plot of the substance concentration versus the percentage inhibition.

The in vitro effect of test substances on recombinant PDE3B, PDE4B, PDE7B, PDE8A, PDE10A and PDE11A is determined in accordance with the assay protocol described above for PDE9A with the following adaptations: [5',8-$^3$H] adenosine 3',5'-cyclic phosphate (1 μCi/μL; Amersham Pharmacia Biotech., Piscataway, N.J.) is used as substrate. Addition of an inhibitor solution to stop the reaction is unnecessary. Instead, the incubation of substrate and PDE is followed immediately by addition of the yttrium scintillation proximity beads as described above and thus the reaction is stopped. To determine a corresponding effect on recombinant PDE1C, PDE2A and PDE5A, the protocol is additionally adapted as follows: with PDE1C, additionally 10$^{-7}$ M calmodulin and 3 mM CaCl$_2$ are added to the reaction mixture. PDE2A is stimulated in the assay by adding 1 μM cGMP and is assayed with a BSA concentration of 0.01%. The substrate employed for PDE1C and PDE2A is [5',8-$^3$H] adenosine 3',5'-cyclic phosphate (1 μCi/μL; Amersham Pharmacia Biotech., Piscataway, N.J.), and for PDE5A is [8-$^3$H] guanosine 3',5'-cyclic phosphate (1 μCi/μL; Amersham Pharmacia Biotech., Piscataway, N.J.).

The PDE9A-inhibiting effect of the compounds of the invention can be shown on the basis of the following examples in Tables 1 and 2:

TABLE 1

Inhibition of PDE isoenzymes by Example 3

| Isoenzyme | Species | IC$_{50}$ [nM] |
|---|---|---|
| PDE1C | human | 720 |
| PDE2A | human | >4000 |
| PDE3B | human | >4000 |
| PDE4B | human | >4000 |
| PDE5A | human | >4000 |
| PDE7B | human | >4000 |
| PDE8A | human | >4000 |
| PDE9A | human | 110 |
| PDE10A | human | >4000 |

TABLE 2

PDE9A-inhibiting effect of the compounds of the invention

| Example | IC$_{50}$ [nM] |
|---|---|
| 1 | 5 |
| 3 | 110 |
| 4 | 30 |
| 6 | 6 |
| 12 | 65 |
| 17 | 86 |
| 19 | 390 |

Increasing the Intracellular Neuronal cGMP Concentration in Cell Cultures

PDE9A inhibitors increase the intracellular neuronal cGMP in cultivated primary cortical neurons.

Rat embryos (embryonic day E17-E19) were decapitated, and the heads were transferred into dissection dishes filled with dissection medium (DMEM, penicillin/streptomycin; both from Gibco). The scalp and the roof of the scalp were removed, and the exposed brains were transferred into another Petri dish with dissection medium. Using a binocular microscope and two forceps, the cerebrum (cortex) was isolated and cooled to 4° C. with ice. This dissection and the isolation of the cortical neurons was then carried out in accordance with a standard protocol using the Papain kit (Worthington Biochemical Corporation, Lakewood, N.J. 08701, USA) (Huettner et al. *J. Neurosci.* 1986, 6, 3044-3060). The mechanically isolated cortical neurons were cultivated at 150,000 cells/well in 200 μl of neurobasal naedium/well (neurobasal; B27 supplement; 2 mM L-glutamine; in the presence of penicillin/streptomycin; all agents from Gibco) in 96-well plates (pretreated with poly-D-lysine/100 μg/ml for 30 min) under standard conditions (37° C., 5% CO$_2$) for 7 days. After 7 days, the medium was removed and the cells were washed with HBSS buffer (Hank's balanced salt solution, Gibco/BRL). Subsequently, 100 μl of compound of the invention dissolved in HBSS buffer (previously dissolved in 100% DMSO: 10 mM) are put on the cells. Subsequently, a further 100 μl of HBSS buffer are added, so that the final concentration of the compounds of the invention is for example in a range from 20 nM to 10 μM, and incubated at 37° C. for 20 min. The assay buffer is then completely removed. Subsequently, the cells are lyzed in 200 μl of lysis buffer (cGMP kit code RPN 226; from Amersham Pharmacia Biotech.), and the cGMP concentration was measured as stated by the manufacturer. All measurements are carried out in triplicate. Statistical analysis takes place using Prism Software Version 2.0 (GraphPad Software Inc., San Diego, Calif. USA).

Incubation of the primary neurons with the compounds of the invention led to an increase in the cGMP content.

Long-Term Potentiation

Long-term potentiation is regarded as a cellular correlate of learning and memory processes. The following method can be used to determine whether PDE 9 inhibition has an influence on long-term potentiation:

Rat hippocampi are placed at an angle of about 70 degrees to the cutting blade (chopper). 400 μm-thick slices of the hippocampus are prepared. The slices are removed from the blade using a very soft, thoroughly wetted brush (marten hair) and transferred into a glass vessel with cold nutrient solution (124 mM NaCl, 4.9 mM KCl, 1.3 mM MgSO$_4$×7 H$_2$O, 2.5 mM CaCl$_2$ anhydrous, 1.2 mM KH$_2$PO$_4$, 25.6 mM NaHCO$_3$, 10 mM glucose, pH 7.4) gassed with 95% O$_2$/5% CO$_2$. During the measurement, the slices are kept in a temperature-controlled chamber under a 1-3 mm-high liquid level. The flow rate is 2.5 ml/min. The preliminary gassing takes place under a slightly elevated pressure (about 1 atm) and through a microneedle in the prechamber. The slice chamber is connected to the prechamber in such a way that a minicirculation can be maintained. The minicirculation is driven by the 95% O$_2$/5% CO$_2$ flowing out through the microneedle. The freshly prepared hippocampus slices are adapted in the slice chamber at 33° C. for at least 1 hour.

The stimulus level is chosen so that the focal excitatory postsynaptic potentials (fEPSP) are 30% of the maximum excitatory postsynaptic potential (EPSP). A monopolar stimulation electrode consisting of lacquered stainless steel, and a constant-current biphasic stimulus generator (AM Systems 2100) are used for local stimulation of the Schaffer collaterals (voltage: 1-5 V, pulse width of one polarity 0.1 ms, total pulse 0.2 ms). Glass electrodes (borosilicate glass with filament, 1-5 MOhm, diameter: 1.5 mm, tip diameter: 3-20 µm), filled with normal nutrient solution, are used to record the excitatory postsynaptic potentials (fEPSP) from the stratum radiatum. The field potentials are measured versus a chlorinated silver reference electrode located at the edge of the slice chamber using a DC voltage amplifier. The field potentials are filtered through a low-pass filter (5 kHz). The slope of the fEPSPs (fEPSP slope) is determined for the statistical analysis of the experiments. The recording, analysis and control of the experiment takes place with the aid of a software program (PWIN) which was developed in the Department of Neurophysiology. The formation of the average fEPSP slopes at the respective time points and construction of the diagrams takes place with the aid of the EXCEL software, with automatic data recording by an appropriate macro.

Superfusion of the hippocampus slices with a 10 µM solution of the compounds of the invention leads to a significant increase in the LTP.

Social Recognition Test

The social recognition test is a learning and memory test. It measures the ability of rats to distinguish between known and unknown members of the same species. This test is therefore suitable for examining the learning- or memory-improving effect of the substances of the invention.

Adult rats housed in groups are placed singly in test cages 30 min before the start of the test. Four min before the start of the test, the test animal is put in an observation box. After this adaptation time, a juvenile animal is put in with the test animal and the absolute time for which the adult animal inspects the young one is measured for 2 min (trial 1). All behaviors clearly directed at the young animal are measured, i.e. anogenital inspection, pursuit and grooming, during which the old animal was no further than 1 cm from the young animal. The juvenile is then removed, and the adult is treated with a compound of the invention or vehicle and subsequently returned to its own cage. The test is repeated after a retention time of 24 hours (trial 2). A diminished social interaction time compared with trial 1 indicates that the adult rat remembers the young animal.

The adult animals receive intraperitoneal injections directly following trial 1 either with vehicle (10% ethanol, 20% Solutol, 70% physiological saline) or 0.1 mg/kg, 0.3 mg/kg, 1.0 mg/kg or 3.0 mg/kg compound of the invention dissolved in 10% ethanol, 20% Solutel, 70% physiological saline. Vehicle-treated rats show no reduction in the social interaction time in trial 2 compared with trial 1. They have consequently forgotten that they have already had contact with the young animal. Surprisingly, the social interaction time in the second run after treatment with the compounds of the invention is significantly reduced compared with those treated with vehicle. This means that the substance-treated rats have remembered the juvenile animal and thus the compounds of the invention display an improving effect on learning and memory.

The present invention further relates to medicaments comprising at least one compound of the invention and at least one or more other active ingredients, in particular for the treatment and/or prophylaxis of the aforementioned disorders.

The compounds of the invention may have systemic and/or local effects. They can for this purpose be administered in a suitable way, such as, for example, by the oral, parenteral, pulmonary, nasal, sublingual, lingual, buccal, rectal, dermal, transdermal, conjunctival or otic route or as implant or stent.

The compounds of the invention can be administered in suitable administration forms for these administration routes.

Administration forms suitable for oral administration are those which function according to the state of the art and deliver the compounds of the invention in a rapid and/or modified way, and which contain the compounds of the invention in crystalline and/or amorphized and/or dissolved form, such as, for example, tablets (uncoated or coated tablets, for example with coatings which are resistant to gastric juice or dissolve slowly or are insoluble and which control the release of the compound of the invention), tablets which rapidly disintegrate in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, injection and infusion preparations in the form of solutions, suspensions, emulsions, lyophilisates or sterile powders.

Examples suitable for other administration routes are medicinal farms for inhalation (inter alia powder inhalators, nebulizers), nasal drops, solutions, sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

The compounds of the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and masking tastes and/or odors.

The present invention further relates to medicaments which comprise at least one compound of the invention, normally together with one or more inert, non-toxic, pharmaceutically suitable excipients, and to the use thereof for the aforementioned purposes.

It has generally proved advantageous on parenteral administration to administer amounts of about 0.001 to 10 mg/kg of body weight per day to achieve effective results. The amount per day on oral administration is about 0.005 to 3 mg/kg of body weight.

It may nevertheless be necessary to deviate from the stated amounts, in particular as a function of body weight, administration route, individual behavior toward the active ingredient, type of preparation and time or interval over which administration takes place. Thus, it may in some cases be sufficient to make do with less than the aforementioned minimum amount, whereas in other cases the stated upper limit must be exceeded. Where larger amounts are administered, it may be advisable to divide them into a plurality of single doses over the day.

The percentage data in the following tests and examples are, unless indicated otherwise, percentages by weight; parts are parts by weight. Solvent ratios, dilution ratios and concentration data for liquid/liquid solutions are in each case based on volume.

| Abbreviations used: | |
|---|---|
| BSA | bovine serum albumin |
| DCI | direct chemical ionization (in MS) |
| DMSO | dimethyl sulfoxide |
| EDTA | ethylenediaminetetraacetic acid |
| equiv. | equivalent(s) |
| ESI | electrospray ionization (in MS) |
| HATU | O-(7-azabenzotriazol-1-yl)-N,N,N',N'-tetramethyluronium hexafluorophosphate |
| Lit. | literature (reference) |
| m.p. | melting point |
| MS | mass spectroscopy |
| NMR | nuclear magnetic resonance spectroscopy |
| Tris | tris(hydroxymethyl)aminomethane |

Starting Compounds

EXAMPLE 1A

5-Amino-1-cyclohexyl-1H-pyrazole-4-carbonitrile

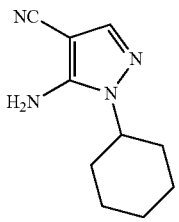

First ethoxymethylenemalononitrile (2.43 g, 19.9 mmol) and then 8 ml of triethylamine are added to a solution of cyclohexylhydrazine hydrochloride (3 g, 19.9 mmol) in 36 ml of ethanol at room temperature. The mixture is refluxed for 20 min and then cooled. The solvent is stripped off in a rotary evaporator, and the residue is taken up in DCM, washed with aqueous sodium bicarbonate solution, dried over sodium sulfate, filtered and concentrated in vacuo. The crude product is chromatographed on silica gel (mobile phase: dichloromethane/methanol 0-10%).

Yield: 1.95 g (51% of theory)
MS (DCI): m/z=191 (M+H)$^+$
$^1$H-NMR (200 MHz, DMSO-d$_6$): δ=7.5 (s, 1H), 6.5 (s, 2H), 4.0 (m, 1H), 1.95-1.05 (m, 10H) ppm.

EXAMPLE 2A

5-Amino-1-cyclopentyl-1H-pyrazole-4-carbonitrile

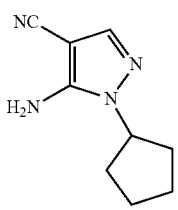 [SMILES: N#Cc1cnn(C2CCCC2)c1N]

Preparation takes place in analogy to the method for Example 1A.
MS (ESI): m/z=177 (M+H)$^+$
$^1$H-NMR (200 MHz, CDCl$_3$): δ=7.5 (s, 1H), 4.45 (br. s, 2H), 4.35 (m, 1H), 2.2-1.55 (m, 6H) ppm.

EXAMPLE 3A

5-Amino-1-(1-ethylpropyl)-1H-pyrazole-4-carbonitrile

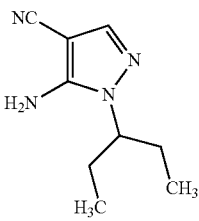

Preparation takes place in analogy to the method for Example 1A.
MS (ESI): m/z=179 (M+H)$^+$
$^1$H-NMR (300 MHz, DMSO-d$_6$): δ=7.55 (s, 1H), 6.45 (s, 2H), 4.0 (m, 1H), 1.8-1.55 (m, 4H), 0.65 (t, 6H) ppm.

EXAMPLE 4A

5-Amino-1-cyclohexyl-1H-pyrazole-4-carboxamide

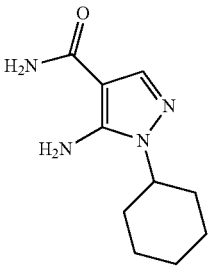 [SMILES: NC(=O)c1cnn(C2CCCCC2)c1N]

18 ml of 30% strength hydrogen peroxide solution are added to a solution of 5-amino-1-cyclohexyl-1H-pyrazole-4-carbonitrile (1.86 g, 9.81 mmol) in a mixture of 73 mi of ethanol and 90 ml of concentrated aqueous ammonia solution at room temperature, and the mixture is stirred at room temperature for 1 h. The nonaqueous solvents are then stripped off in a rotary evaporator. The product precipitates as solids from the remaining mixture and is filtered off with suction, washed with a little water and dried under high vacuum.

Yield: 1.77 g (86% of theory)
MS (DCI): m/z=209 (M+H)$^+$
$^1$H-NMR (300 MHz, DMSO-d$_6$): δ=7.6 (s, 1H), 7.3-6.4 (broad, 2H), 6.1 (s, 2H), 3.95 (m, 1H), 1.95-1.05 (m, 10H) ppm.

EXAMPLE 5A

5-Amino-1-cyclopentyl-1H-pyrazole-4-carboxamide

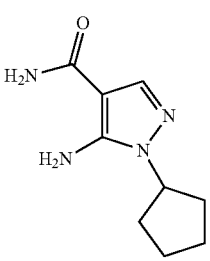 [SMILES: NC(=O)c1cnn(C2CCCC2)c1N]

Preparation takes place in analogy to the method for Example 4A.

MS (ESI): m/z=195 (M+H)+

1H-NMR (200 MHz, CDCl3): δ=7.5 (s, 1H), 5.6-4.8 (broad, 4H), 4.35 (m, 1H), 2.2-1.55 (m, 8H) ppm.

EXAMPLE 6A

5-Amino-1-(1-ethylpropyl)-1H-pyrazole-4-carboxamide

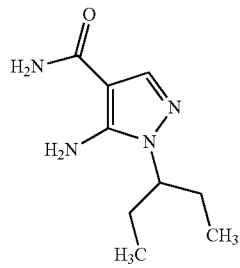

Preparation takes place in analogy to the method for Example 4A.

MS (ESI): m/z=197 (M+H)+

1H-NMR (300 MHz, DMSO-d6): δ=7.65 (s, 1H), 6.9 (br. s, 2H), 6.1 (s, 2H), 3.9 (m, 1H), 1.85-1.6 (m, 4H), 0.7 (t, 6H) ppm.

EXAMPLARY EMBODIMENTS

Example 1

6-(Cyclohexylmethyl)-1-cyclopentyl-1,5-dihydro-4H-pyrazolo[3,4-d]pyrimidin-4-one

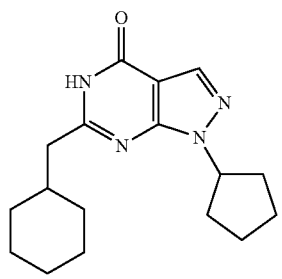 [SMILES: O=c1[nH]c(CC2CCCCC2)nc2c1cnn2C1CCCC1]

Under argon, 75 mg (039 mmol) of 5-amino-1-cyclopentyl-1H-pyrazole-4-carboxamide and 183 mg (1.16 mmol, 3 equiv.) of methyl cyclohexylacetate are introduced into 1.5 ml of absolute ethanol. At 0° C., 54 mg of sodium hydride (60% dispersion in mineral oil; L35 mmol, 15 equiv.) are slowly added in a countercurrent of argon. The resulting mixture is slowly heated and stirred under reflux for 18 h. For workup, 20 ml of water are added, and the mixture is extracted several times with ethyl acetate. The combined organic phases are dried over sodium sulfate and concentrated in vacuo. The crude product is purified by preparative HPLC.

Yield 36 mg (31% of theory)

MS (ESI): m/z=301 (M+H)+ m.p.: 147° C.

1H-NMR (300 MHz, DMSO-d6): δ=11.95 (s, 1H), 8.0 (s, 1H), 5.1 (m, 1H), 2.5 (d, 2H), 2.15-1.75 (m, 7H), 1.75-1.55 (m, 7H), 1.3-0.9 (m, 5H) ppm.

Example 2

1-Cyclopentyl-6-(3-hydroxypropyl)-1,5-dihydro-4H-pyrazolo[3,4-d]pyrimidin-4-one

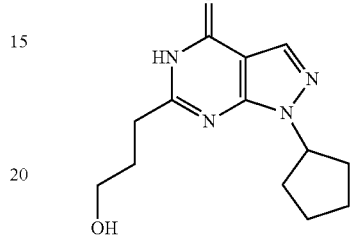

The product is obtained in analogy to Example 1 starting from 75 mg (0.39 mmol) of 5-amino-1-cyclopentyl-1H-pyrazole-4-carboxamide and 140 mg (1.16 mmol) of methyl 4-hydroxybutyrate.

Yield: 85 mg (84% of theory)

MS (DCI): m/z=263 (M+H)+ m.p.: 138° C.

1H-NMR (200 MHz, DMSO-d6): δ=8.0 (s, 1H), 5.1 (m, 1H), 3.5 (t, 2H, J=6.5 Hz), 2.65 (t, 2H, J=7.5 Hz), 2.2-1.55 (m, 10H) ppm.

Example 3

6-(Cyclohexylmethyl)-1-(1-ethylpropyl)-1,5-dihydro-4H-pyrazolo[3,4-d]pyrimidin-4-one

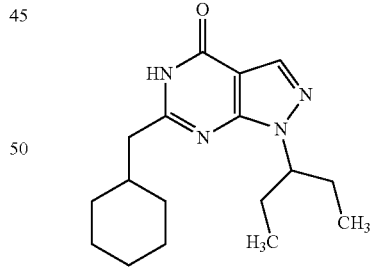

The product is obtained in analogy to Example 1 starting from 200 mg (1.02 mmol) of 5-amino-1-(1-ethylpropyl)-1H-pyrazol-4-carboxamide and 482 mg (3.06 mmol) of methyl cyclohexylacetate.

Yield: 146 mg (47% of theory)

MS (ESI): m/z=303 (M+H)+ m.p.: 122° C.

1H-NMR (200 MHz, DMSO-d6): δ=12.0 (s, 1H), 8.0 (s, 1H), 4.45 (m, 1H), 2.5 (m, 2H), 2.0-1.5 (m, 10H), 1.4-0.9 (m, 5H), 0.6 (t, 6H, J=7.5 Hz) ppm.

Example 4

1-Cyclopentyl-6-(2-methylbutyl)-1,5-dihydro-4H-pyrazolo[3,4-d]pyrimidin-4-one

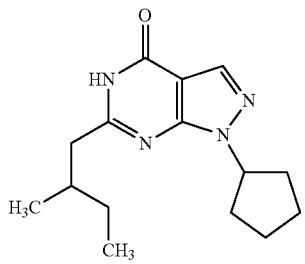 [SMILES: CCC(C)Cc1nc2c(cnn2C2CCCC2)c(=O)[nH]1]

The product is obtained in analogy to Example 1 starting from 200 mg (1.01 mmol) of 5-amino-1-cyclopentyl-1H-pyrazole-4-carboxamide and 450 mg (3.03 mmol) of ethyl 3-methylvalerate.

Yield: 88 mg (32% of theory)

MS (DCI): m/z=275 (M+H)$^+$ m.p.: 86° C.

$^1$H-NMR (300 MHz, DMSO-d$_6$): δ=12.0 (s, 1H), 8.0 (s, 1H), 5.1 (m, 1H), 2.65 (dd, 1H), 2.45 (dd, 1H), 2.15-1.8 (m, 7H), 1.7 (m, 2H), 1.45-1.15 (m, 2H), 0.9 (m, 6H) ppm.

Example 5

1-Cyclopentyl-6-(3-methylbutyl)-1,5-dihydro-4H-pyrazolo[3,4-d]pyrimidin-4-one

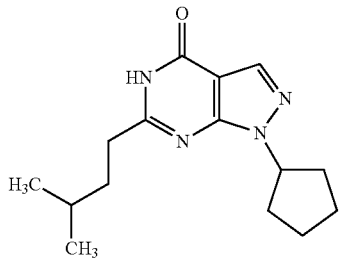 [SMILES: CC(C)CCc1nc2c(cnn2C2CCCC2)c(=O)[nH]1]

The product is obtained in analogy to Example 1 starting from 200 mg (1.01 mmol) of 5-amino-1-cyclopentyl-1H-pyrazole-4-carboxamide and 450 mg (3.03 mmol) of ethyl 4-methylvalerate.

Yield: 165 mg (60% of theory)

MS (ESI): m/z=275 (M+H)$^+$ m.p.: 133° C.

$^1$H-NMR (200 MHz, DMSO-d$_6$): δ=12.0 (s, 1H), 8.0 (s, 1H), 5.1 (m, 1H), 2.6 (m, 2H), 2.2-1.5 (m, 11H), 0.9 (d, 6H, J=6.5 Hz) ppm.

Example 6

6-(2-Cyclopenten-1-ylmethyl)-1-cyclopentyl-1,5-dihydro-4H-pyrazolo[3,4-d]pyrimidin-4-one

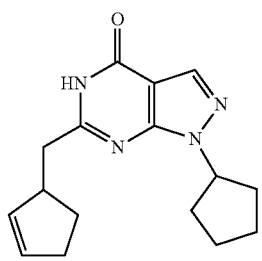 [SMILES: O=c1[nH]c(CC2C=CCC2)nc2c1cnn2C1CCCC1]

The product is obtained in analogy to Example 1 starting from 200 mg (1.01 mmol) of 5-amino-1-cyclopentyl-1H-pyrazole-4-carboxamide and 446 mg (1.82 mmol, 95% pure) of methyl 2-cyclopenten-1-ylacetate (Lit: Roenn et al., Tetrahedron Lett. 1995, 36, 7749).

Yield: 86 mg (30% of theory)

MS (ESI): m/z=285 (M+H)$^+$ m.p.: 166° C.

$^1$H-NMR (200 MHz, DMSO-d$_6$): δ=12.0 (s, 1H), 8.0 (s, 1H), 5.75 (m, 2H), 5.1 (m, 1H), 3.15 (m, 1H), 2.8-2.5 (m, 2H), 2.45-1.45 (m, 12H) ppm.

Example 7

1-(1-Ethylpropyl)-6-(2-methylbutyl)-1,5-dihydro-4H-pyrazolo[3,4-d]pyrimidin-4-one

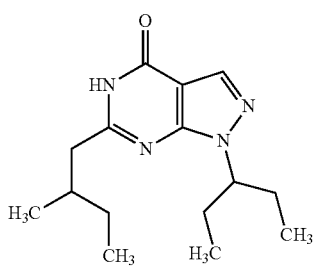

The product is obtained in analogy to Example 1 starting from 200 mg (1.0 mmol) of 5-amino-1-(1-ethylpropyl)-1H-pyrazole-4-carboxamide and 445 mg (3.0 mmol) of ethyl 3-methylvalerate.

Yield: 99 mg (36% of theory)

MS (ESI): m/z=277 (M+H)$^+$ m.p.: 121° C.

$^1$H-NMR (300 MHz, DMSO-d$_6$): δ=12.0 (s, 1H), 8.0 (s, 1H), 4.5 (m, 1H), 2.6 (dd, 1H), 2.45 (dd, 1H), 2.05-1.7 (m, 5H), 1.45-1.15 (m, 2H), 0.9 (m, 6H), 0.65 (t, 6H, J=7.5 Hz) ppm.

Example 8

1-(1-Ethylpropyl)-6-isopentyl-1,5-dihydro-4H-pyrazolo[3,4-d]pyrimidin-4-one

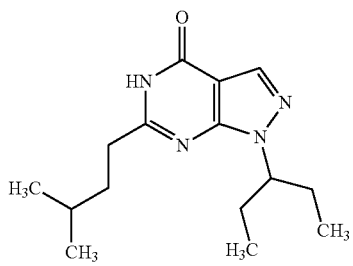

The product is obtained in analogy to Example 1 starting from 200 mg (1.0 mmol) of 5-amino-1-(1-ethylpropyl)-1H-pyrazole-4-carboxamide and 445 mg (3.0 mmol) of ethyl 4-methylvalerate.

Yield: 127 mg (46% of theory)

MS (ESI): m/z=277 (M+H)$^+$ m.p.: 127° C.

$^1$H-NMR (300 MHz, DMSO-d$_6$): δ=12.0 (s, 1H), 8.0 (s, 1H), 4.45 (m, 1H), 2.65 (m, 2H), 2.0-1.8 (m, 4H), 1.7-1.5 (m, 3H), 0.9 (d, 6H, J=7 Hz), 0.6 (t, 6H, J=6 Hz) ppm.

Example 9

1-(1-Ethylpropyl)-6-isobutyl-1,5-dihydro-4H-pyrazolo[3,4-d]pyrimidin-4-one

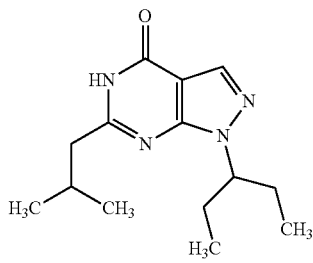

The product is obtained in analogy to Example 1 starting from 200 mg (1.0 mmol) of 5-amino-1-(1-ethylpropyl)-1H-pyrazole-4-carboxamide and 464 mg (3.5 mmol) of ethyl 3-methylbutyrate.

Yield: 127 mg (48% of theory)

MS (ESI): m/z=263 (M+H)$^+$ m.p.: 161° C.

$^1$H-NMR (300 MHz, DMSO-d$_6$): δ=12.0 (s, 1H), 8.0 (s, 1H), 4.45 (m, 1H), 2.5 (m, 2H), 2.15 (m, 1H), 1.95-1.75 (m, 4H), 0.9 (d, 6H, J=7 Hz), 0.55 (t, 6H, J=7.5 Hz) ppm.

Example 10

1-(1-Ethylpropyl)-6-propyl-1,5-dihydro-4H-pyrazolo[3,4-d]pyrimidin-4-one

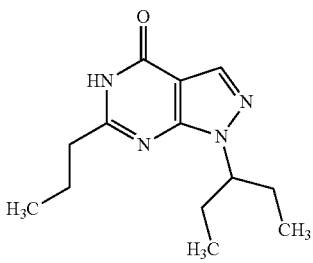 [SMILES: CCCc1nc2c(cnn2C(CC)CC)c(=O)[nH]1]

The product is obtained in analogy to Example 1 starting from 200 mg (1.0 mmol) of 5-amino-1-(1-ethylpropyl)-1H-pyrazole-4-carboxamide and 410 mg (3.5 mmol) of ethylbutyrate.

Yield: 159 mg (64% of theory)

MS (ESI): m/z=249 (M+H)$^+$ m.p.: 127° C.

$^1$H-NMR (300 MHz, DMSO-d$_6$): δ=11.95 (s, 1H), 8.0 (s, 1H), 4.5 (m, 1H), 2.6 (t, 2H, J=7.5 Hz), 2.0-1.65 (m, 6H), 0.9 (t, 3H, J=7.5 Hz), 0.6 (t, 6H, J=7.5 Hz) ppm.

Example 11

1-(1-Ethylpropyl)-6-(tetrahydro-2-furanylmethyl)-1,5-dihydro-4H-pyrazolo[3,4-d]-pyrimidin-4-one

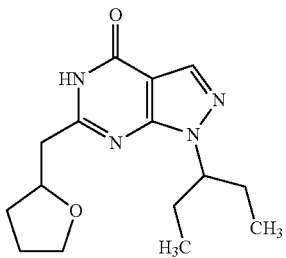 [SMILES: CCC(CC)n1ncc2c(=O)[nH]c(CC3CCCO3)nc21]

The product is obtained in analogy to Example 1 starting from 200 mg (1.0 mmol) of 5-amino-1-(1-ethylpropyl)-1H-pyrazole-4-carboxamide and 553 mg (3.5 mmol) of ethyl tetrahydrofuran-2-ylacetate.

Yield: 202 mg (68% of theory)

MS (ESI): m/z=291 (M+H)$^+$ m.p: 136° C.

$^1$H-NMR (200 MHz, DMSO-d$_6$): δ=12.0 (s, 1H), 8.0 (s, 1H), 4.45 (m, 1H), 4.25 (m, 1H), 3.75 (m, 1H), 3.6 (m, 1H), 2.8 (m, 2H), 2.1-1.55 (m, 8H), 0.6 (t, 6H, J=7.5 Hz) ppm.

Example 12

6-(2-Cyclopenten-1-ylmethyl)-1-(1-ethylpropyl)-1,5-dihydro-4H-pyrazolo[3,4-d]-pyrimidin-4-one

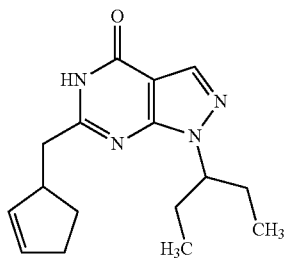 [SMILES: CCC(CC)n1ncc2c(=O)[nH]c(CC3C=CCC3)nc21]

The product is obtained in analogy to Example 1 starting from 200 mg (1.0 mmol) of 5-amino-1-(1-ethylpropyl)-1H-pyrazole-4-carboxamide and 490 mg (3.5 mmol) of methyl 2-cyclopenten-1-ylacetate (Lit.: Roenn et al., Tetrahedron Lett 1995, 36, 7749).

Yield: 111 mg (39% of theory)

MS (ESI): m/z=287 (M+H)$^+$ m.p.: 128° C.

$^1$H-NMR (200 MHz, DMSO-d$_6$): δ=12.0 (s, 1H), 8.0 (s, 1H), 5.8-5.65 (m, 2H), 4.5 (m, 1H), 3.2 (m, 1H), 2.8-2.55 (m, 2H), 2.3 (m, 2H), 2.15-1.8 (m, 5H), 1.55 (m, 1H), 0.65 (t, 6H, J=7.5 Hz) ppm.

Example 13

Ethyl 4-[1-(1-ethylpropyl)-4-oxo-4,5-dihydro-1H-pyrazolo[3,4-d]pyrimidin-6-yl]-butyrate

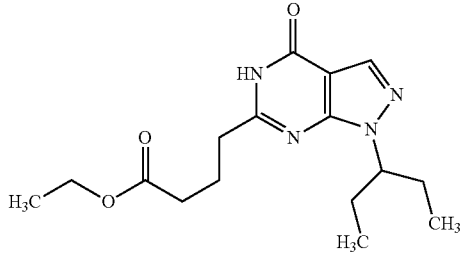 [SMILES: CCOC(=O)CCCc1nc2c(cnn2C(CC)CC)c(=O)[nH]1]

The product is obtained in analogy to Example 1 starting from 200 mg (1.0 mmol) of 5-amino-1-(1-ethylpropyl)-1H-pyrazole-4-carboxamide and 1.13 g (6.0 mmol) of diethyl glutarate.

Yield: 46 mg (13% of theory)

MS (ESI): m/z=321 (M+H)$^+$ $^1$H-NMR (200 MHz, DMSO-d$_6$): δ=12.0 (s, 1H), 8.0 (s, 1H), 4.5 (m, 1H), 4.2 (q, 2H, J=7 Hz), 2.7 (t, 2H, J=7.5 Hz), 2.4 (t, 2H, J=7 Hz), 2.1-1.75 (m, 6H), 1.2 (t, 3H, J=7 Hz), 0.65 (t, 6H, J=7.5 Hz) ppm.

Example 14

Ethyl 4-[1-(1-ethylpropyl)-4-oxo-4,5-dihydro-1H-pyrazolo[3,4-d]pyrimidin-6-yl]-propionate

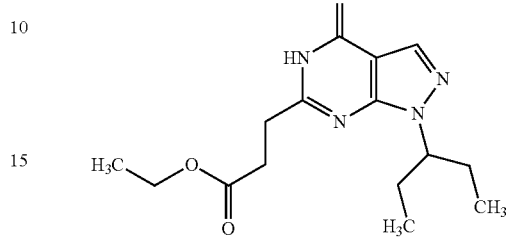

The product is obtained in analogy to Example 1 starting from 200 mg (1.0 mmol) of 5-amino-1-(1-ethylpropyl)-1H-pyrazole-4-carboxamide and 1.04 g (6 mmol) of diethyl succinate.

Yield: 176 mg (56% of theory)

MS (ESI): m/z=307 (M+H)$^+$ m.p.: 118° C.

$^1$H-NMR (200 MHz, DMSO-d$_6$): δ=12.1 (s, 1H), 8.0 (s, 1H), 4.4 (m, 1H), 4.0 (q, 2H, J=7 Hz), 2.9 (m, 2H), 2.8 (m, 2H), 2.0-1.7 (m, 4H), 1.2 (t, 3H, J=7 Hz), 0.6 (t, 6H, J=7.5 Hz) ppm.

Example 15

1-Cyclopentyl-6-[(4-methylcyclohexyl)methyl]-1,5-dihydro-4H-pyrazolo[3,4-d]-pyrimidin-4-one

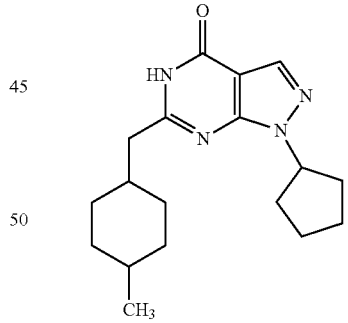

The product is obtained in analogy to Example 1 starting from 200 mg (1.0 mmol) of 5-amino-1-cyclopentyl-1H-pyrazole-4-carboxamide and 664 mg (3.5 mmol) of ethyl (4-methylcyclohexyl)acetate (cis/trans mixture). The product is in the form of a mixture of the cis and trans isomers.

Yield: 131 mg (41% of theory)

MS (ESI): m/z=315 (M+H)$^+$ m.p.: 126° C.

$^1$H-NMR (200 MHz, DMSO-d$_6$): δ=12.0 (s, 1H), 8.0 (s, 1H), 5.1 (m, 1H), 2.6 (d, 2H, J=7 Hz), 2.2-0.8 (m, 21H) ppm.

Example 16

1-(1-Ethylpropyl)-6-[(4-methylcyclohexyl)methyl]-1,5-dihydro-4H-pyrazolo[3,4-d]-pyrimidin-4-one

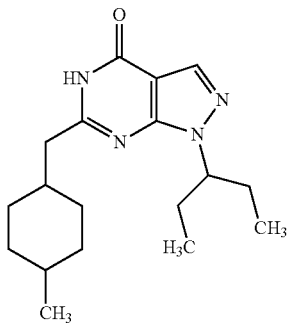 [SMILES: CCC(CC)n1ncc2c(=O)[nH]c(CC3CCC(C)CC3)nc21]

The product is obtained in analogy to Example 1 starting from 200 mg (1.0 mmol) of 5-amino-1-(1-ethylpropyl)-1H-pyrazole-4-carboxamide and 413 mg (2.2 mmol) of ethyl (4-methylcyclohexyl)acetate (cis/trans mixture). The product is in the form of a mixture of the cis and trans isomers.

Yield: 60 mg (19% of theory)

MS (ESI): m/z=317 (M+H)$^+$ $^1$H-NMR (200 MHz, DMSO-d$_6$): δ=12.0 (s, 1H), 8.0 (s, 1H), 4.45 (m, 1H), 2.6 (d, 2H, J==7 Hz), 2.2-0.8 (m, 17H), 0.6 (t, 6H, J=7.5 Hz) ppm.

Example 17

1-Cyclopentyl-6-(tetrahydro-2-furanylmethyl)-1,5-dihydro-4H-pyrazolo[3,4-d]pyrimidin-4-one

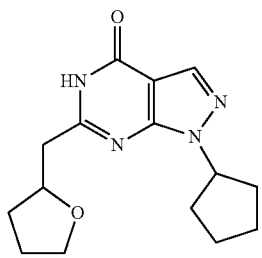 [SMILES: O=c1[nH]c(CC2CCCO2)nc2c1cnn2C1CCCC1]

The product is obtained in analogy to Example 1 starting from 200 mg (1.0 mmol) of 5-amino-1-(1-ethylpropyl)-1H-pyrazole-4-carboxamide and 559 mg (3.5 mmol) of ethyl tetrahydrofuran-2-ylacetate.

Yield: 175 mg (60% of theory)

MS (ESI): m/z=289 (M+H)$^+$ m.p.: 179° C. $^1$H-NMR. (200 MHz, DMSO-d$_6$): δ=11.95 (s, 1H), 8.0 (s, 1H), 5.1 (m, 1H), 4.3 (m, 1H), 3.8 (m, 1H), 3.6 (m, 1H), 2.8 (m, 2H), 2.15-1.55 (m, 12H) ppm.

Example 18

Ethyl 4-[1-cyclopentyl-4-oxo-4,5-dihydro-1H-pyrazolo[3,4-d]pyrimidin-6-yl]-propionate

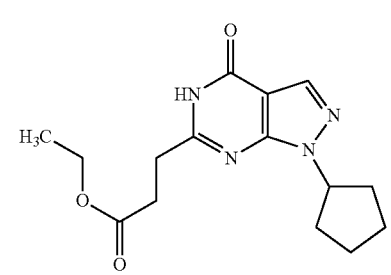 [SMILES: CCOC(=O)CCc1nc2c(cnn2C2CCCC2)c(=O)[nH]1]

The product is obtained in analogy to Example 1 starting from 200 mg (1.0 mmol) of 5-amino-1-cyclopentyl-1H-pyrazole-4-carboxamide and 1.05 g (6.05 mmol) of diethyl succinate.

Yield: 150 mg (49% of theory)

MS (DCI): m/z=305 (M+H)$^+$ m.p.: 185° C.

$^1$H-NMR (200 MHz, DMSO-d$_6$): δ=12.1 (s, 1H), 8.0 (s, 1H), 5.05 (m, 1H), 4.05 (q, 2H, J=7 Hz), 2.9 (m, 2H), 2.8 (m, 2H), 2.15-1.6 (m, 8H), 1.2 (t, 3H, J=7 Hz) ppm.

Example 19

6-(Cyclohexylmethyl)-1-(1-ethylpropyl)-1,5-dihydro-4H-pyrazolo[3,4-d]pyrimidine-4-thione

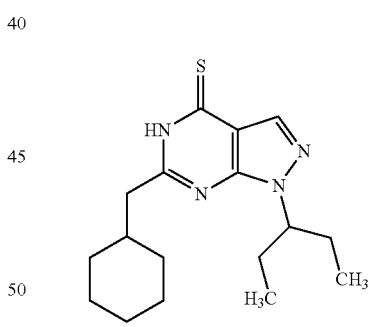

74 mg (0.33 mmol, 2 equiv.) of diphosphorus pentasulfide are added to a solution of 50 mg (0.17 mmol) of 6-(cyclohexylmethyl)-1-(1-ethylpropyl)-1,5-dihydro-4H-pyrazolo[3,4-d]pyrimidin-4-one (Example 3) in 1 ml of pyridine at room temperature, and the mixture is then stirred under reflux overnight. After cooling, the reaction solution is mixed with 20 ml of ice-cold 2.5% strength sodium bicarbonate solution and extracted three times with ethyl acetate. The combined organic phases are washed with saturated brine, dried over sodium sulfate and concentrated in vacuo. The crude product is purified by preparative HPLC.

Yield: 42 mg (80% of theory)

MS (DCI): m/z=319 (M+H)$^+$

¹H-NMR (200 MHz, DMSO-d₆): δ=13.4 (s, 1H), 8.2 (s, 1H), 4.45 (m, 1H), 2.7 (d, 2H, J=7 Hz), 2.0-1.5 (m, 10H), 1.4-0.85 (m, 5H), 0.6 (t, 6H, J=7.5 Hz) ppm.

Example 20

3-(1-Cyclopentyl-4-oxo-4,5-dihydro-1H-pyrazolo[3,4-d]pyrimidin-6-yl)-N-phenyl-propanamide

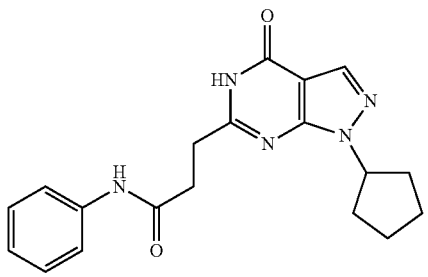 [SMILES: O=C(CCc1nc2c(cnn2C2CCCC2)c(=O)[nH]1)Nc1ccccc1]

A solution of 100 mg (0.33 mmol) of ethyl 4-[1-cyclopentyl-4-oxo-4,5-dihydro-1H-pyrazolo[3,4-d]pyrimidin-6-yl] propionate (Example 18) in a mixture of 1 ml of ethanol and 0.5 ml of 20% strength sodium hydroxide solution is stirred at 60° C. for 1 h. The organic solvent portion is stripped off in a rotary evaporator and the solution is adjusted to pH 3 with 1N hydrochloric acid. The solution is then evaporated to dryness, the residue is stirred with 5 ml of methanol, and the solution is filtered. Stripping off the methanol results in the corresponding carboxylic acid as crude product (90 mg, quantitative).

87 mg (0.31 mmol) of the carboxylic acid obtained in this way are introduced into 6 ml of dichloromethane and firstly 119 mg (0.31 mmol, 1 equiv.) of HATU and then 29 mg (0.31 mmol, 1 equiv.) of aniline and 81 mg (0.63 mmol, 2 equiv.) of N-ethyl-diisopropylamine are added, and the mixture is stirred overnight. For workup, the reaction solution is washed twice with saturated sodium bicarbonate solution, and the organic phase is dried over sodium sulfate and concentrated in vacuo. The crude product is purified by preparative HPLC.

Yield: 25 mg (22% of theory)
MS (ESI): m/z=352 (M+H)⁺
¹H-NMR (200 MHz, DMSO-d₆): δ=12.05 (s, 1H), 10.1 (s, 1H), 8.0 (s, 1H), 7.6 (d, 2H), 7.3 (t, 2H), 7.0 (t, 1H), 5.0 (m, 1H), 3.0 (m, 2H), 2.8 (m, 2H), 2.05-1.4 (m, 8H) ppm.

Example 21

6-(Cyclopentylmethyl)-1-(1-ethylpropyl)-1,5-dihydro-4H-pyrazolo[3,4-d]pyrimidin-4-one

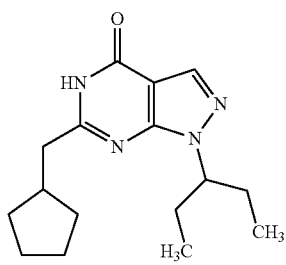

The product is obtained in analogy to Example 1 starting from 150 mg (0.75 mmol) of 5-amino-1-(1-ethylpropyl)-1H-pyrazole-4-carboxamide and 351 mg (2.25 mmol) of ethyl 2-cyclopentylacetate.

Yield: 91 mg (42% of theory)
MS (ESI): m/z=289 (M+H)⁺
m.p.: 156° C.
¹H-NMR (200 MHz, DMSO-d₆): δ=12.0 (s, 1H), 8.0 (s, 1H), 4.45 (m, 1H), 2.7 (d, 2H, J=7.5 Hz), 2.3 (m, 1H), 2.0-1.45 (m, 10H), 1.35-1.1 (m, 2H) 0.6 (t, 6H, J=7.5 Hz) ppm.

Example 22

1-(1-Ethylpropyl)-6-(3,3,3-trifluoro-2-methylpropyl)-1,5-dihydro-4H-pyrazolo[3,4-d]pyrimidin-4-one

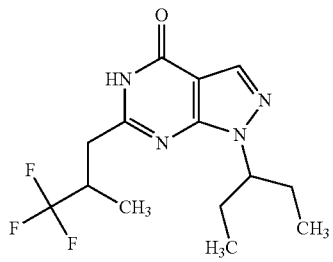 [SMILES: CCC(CC)n1ncc2c(=O)[nH]c(CC(C)C(F)(F)F)nc21]

The product is obtained in analogy to Example 1 starting from 100 mg (0.51 mmol) of 5-amino-1-(1-ethylpropyl)-1H-pyrazole-4-carboxamide and 469 mg (2.55 mmol) of ethyl 3-methyl-4,4,4-trifluorobutyrate.

Yield: 98 mg (61% of theory)
MS (ESI): m/z=317 (M±H)⁺
m.p.: 156° C.
¹H-NMR (200 MHz, DMSO-d₆): δ=12.2 (s, 1H), 8.05 (s, 1H), 4.45 (m, 1H), 3.2-2.9 (m, 2H), 2.7 (m, 1H), 2.0-1.7 (m, 4H), 1.1 (d, 3H), 0.6 (t, 6H) ppm.

Example 23

1-(1-Cyclopentyl)-6-(3,3,3-trifluoro-2-methylpropyl)-1,5-dihydro-4H-pyrazolo[3,4-d]pyrimidin-4-one

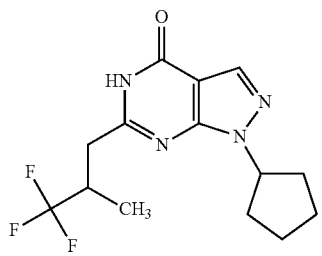 [SMILES: CC(Cc1nc2c(cnn2C2CCCC2)c(=O)[nH]1)C(F)(F)F]

The product is obtained in analogy to Example 1 starting from 100 mg (0.51 mmol) of 5-amino-1-(1-cyclopentyl)-1H-pyrazole-4-carboxamide and 474 mg (2.57 mmol) of ethyl 3-methyl-4,4,4-trifluorobutyrate.

Yield: 119 mg (73% of theory)
MS (ESI): m/z=315 (M+H)⁺
m.p.: 166° C.
¹H-NMR (300 MHz, DMSO-d₆): δ=12.1 (s, 1H), 8.0 (s, 1H), 5.1 (m, 1H), 3.2-2.95 (m, 2H), 2.7 (m, 1H), 2.2-1.6 (m, 8H), 1.1 (d, 3H) ppm.

The invention claimed is:

1. A method for treating an impairment of learning and/or memory comprising administering a compound of the formula (I):

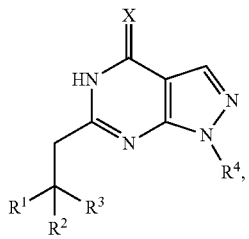

in which
R¹ is $C_1$-$C_6$-alkyl, trifluoromethyl, hydroxy, $C_1$-$C_6$-alkoxy, —C(=O)OR⁵ or —C(=O)NR⁶R⁷, where $C_1$-$C_6$-alkyl is optionally substituted by 1 to 3 radicals independently of one another selected from hydroxy, $C_1$-$C_6$-alkoxy, halogen, trifluoromethyl, trifluoromethoxy, —C(=O)OR⁵ or —C(=O)NR⁶R⁷, and
R⁵ is $C_1$-$C_6$-alkyl,
R⁶ and R⁷ are independently of one another hydrogen, $C_6$-$C_{10}$-aryl, $C_1$-$C_6$-alkyl, or together with the nitrogen atom to which they are bonded form a 4- to 10-membered heterocyclyl,
R² is hydrogen, $C_1$-$C_6$-alkyl, trifluoromethyl or $C_1$-$C_6$-alkoxy,
or
R¹ and R² together with the carbon atom to which they are bonded form $C_3$-$C_8$-cycloalkyl, $C_3$-$C_8$-cycloalkenyl or 4- to 10-membered heterocyclyl, which are optionally substituted by up to 2 substituents selected from $C_1$-$C_6$-alkyl, $C_1$-$C_6$-alkoxy, hydroxy, oxo, or —C(=O)OR⁸, and
R⁸ is $C_1$-$C_6$-alkyl or benzyl,
R³ is hydrogen or $C_1$-$C_6$-alkyl,
R⁴ is pentan-3-yl or $C_3$-$C_6$-cycloalkyl,
X is oxygen or sulfur,
provided that, when R¹ and R² together are unsubstituted cyclohexyl, R⁴ is not pentan-3-yl or cyclopentyl,
or a salt, solvate or solvate of a salt thereof.

2. The method of claim 1, wherein in formula (I),
R¹ is $C_1$-$C_6$-alkyl, hydroxy, $C_1$-$C_6$-alkoxy, —C(=O)OR⁵ or —C(=O)NR⁶R⁷, where $C_1$-$C_6$-alkyl is optionally substituted by hydroxy, $C_1$-$C_6$-alkoxy, —C(=O)OR⁵ or —C(=O)NR⁶R⁷, and
R⁵ is $C_1$-$C_6$-alkyl,
R⁶ and R⁷ are independently of one another hydrogen, $C_6$-$C_{10}$-aryl, $C_1$-$C_6$-alkyl, or together with the nitrogen atom to which they are bonded form a 4- to 10-membered heterocyclyl,
R² is hydrogen, $C_1$-$C_6$-alkyl or $C_1$-$C_6$-alkoxy,
or
R¹ and R² together with the carbon atom to which they are bonded form $C_3$-$C_8$-cycloalkyl, $C_3$-$C_8$-cycloalkenyl or 4- to 10-membered heterocyclyl, which are optionally substituted by up to 2 substituents selected from $C_1$-$C_6$-alkyl, $C_1$-$C_6$-alkoxy, hydroxy, oxo, or —C(=O)OR⁸, and
R⁸ is $C_1$-$C_6$-alkyl or benzyl,
R³ is hydrogen or $C_1$-$C_6$-alkyl,
R⁴ is pentan-3-yl or $C_4$-$C_6$-cycloalkyl,
X is oxygen or sulphur.

3. The method of claim 1, wherein in formula (I):
R¹ is $C_1$-$C_4$-alkyl, hydroxy, $C_1$-$C_4$-alkoxy, —C(=O)OR⁵ or —C(=O)NR⁶R⁷, where $C_1$-$C_4$-alkyl is optionally substituted by hydroxy, trifluoromethyl, $C_1$-$C_4$-alkoxy, —C(=O)OR⁵ or —C(=O)NR⁶R⁷, and
R⁵ is $C_1$-$C_4$-alkyl,
R⁶ and R⁷ are independently of one another hydrogen, phenyl, $C_1$-$C_4$-alkyl, or
together with the nitrogen atom to which they are bonded form a 5- to 6-membered heterocyclyl,
R² is hydrogen, $C_1$-$C_4$-alkyl, trifluoromethyl, $C_1$-$C_4$-alkoxy,
or
R¹ and R² together with the carbon atom to which they are bonded form $C_5$-$C_6$-cycloalkyl, $C_5$-$C_6$-cycloalkenyl or 5- to 6-membered heterocyclyl, which are optionally substituted by up to 2 substituents from the group of $C_1$-$C_4$-alkyl, $C_1$-$C_4$-alkoxy, hydroxy, oxo, —C(=O)OR⁸, and
R⁸ is $C_1$-$C_4$-alkyl or benzyl,
R³ is hydrogen,
R⁴ is pentan-3-yl, $C_5$-$C_6$-cycloalkyl,
X is oxygen or sulphur.

4. The method of claim 1, wherein in formula (I):
R¹ is methyl, ethyl, isopropyl, trifluoromethyl, methoxycarbonyl, ethoxycarbonyl or —C(=O)NR⁶R⁷, where methyl is optionally substituted by methoxycarbonyl or ethoxycarbonyl, and
R⁶ is phenyl and
R⁷ is hydrogen,
R² is hydrogen, methyl or trifluoromethyl, or
R¹ and R² together with the carbon atom to which they are bonded form cyclopentyl, cyclohexyl, cyclopentenyl or tetrahydrofuryl, where cyclohexyl is optionally substituted by methyl, and
R³ is hydrogen,
R⁴ is pentan-3-yl or $C_5$-$C_6$-cycloalkyl,
X is oxygen or sulphur.

5. The method of claim 1, wherein in formula (I):
R¹ is methyl, ethyl, isopropyl, methoxycarbonyl, ethoxycarbonyl or —C(=O)NR⁶R⁷, where methyl is optionally substituted by methoxycarbonyl or ethoxycarbonyl, and
R⁶ is phenyl and
R⁷ is hydrogen,
R² is hydrogen or methyl, or
R¹ and R² together with the carbon atom to which they are bonded form cyclopentyl, cyclohexyl, cyclopentenyl or tetrahydrofuryl, where cyclohexyl is optionally substituted by methyl, and
R³ is hydrogen,
R⁴ is pentan-3-yl or $C_5$-$C_6$-cycloalkyl,
X is oxygen.

6. The method of claim 1, wherein the impairment is a consequence of Alzheimer's disease.

7. The method of claim 1, wherein the compound of formula (I) is selected from the group consisting of the following compounds:

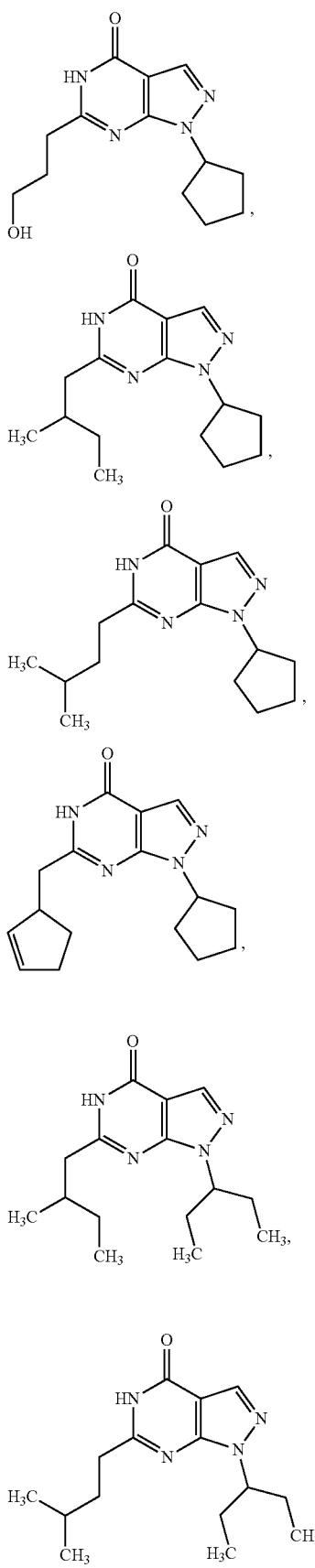
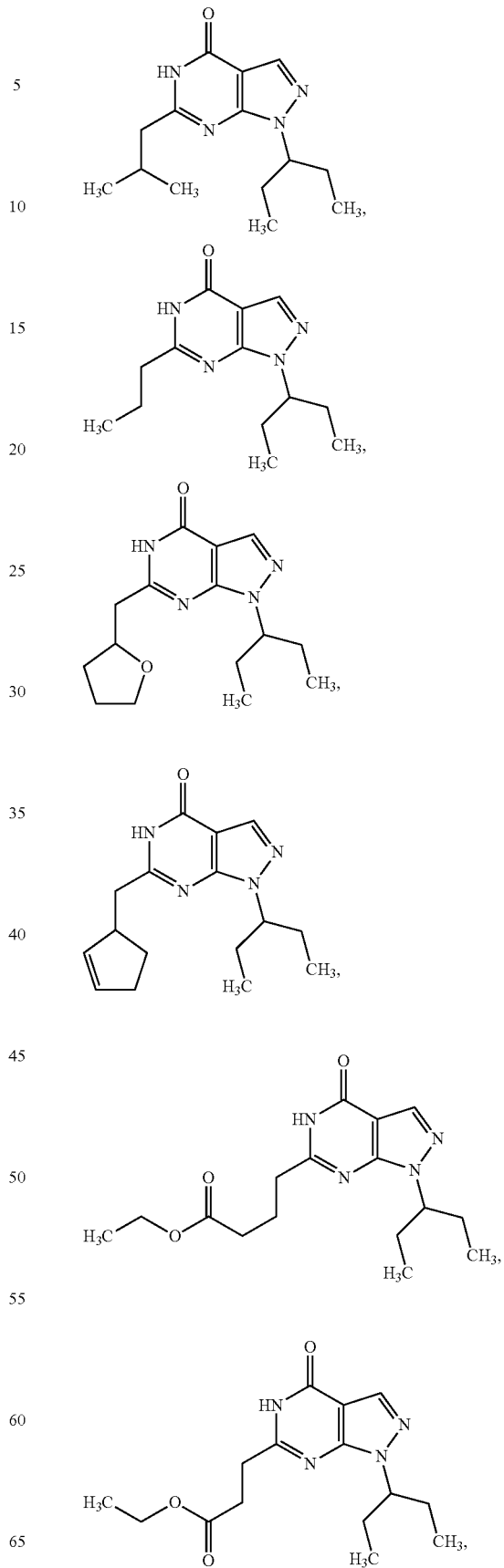

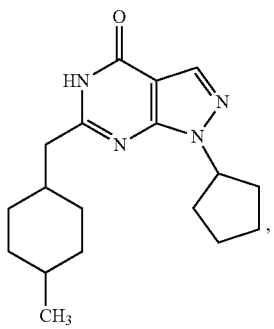
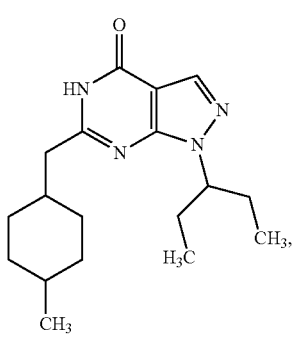
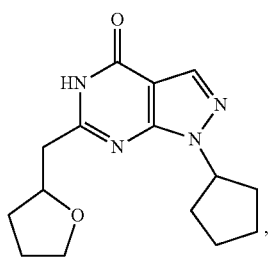
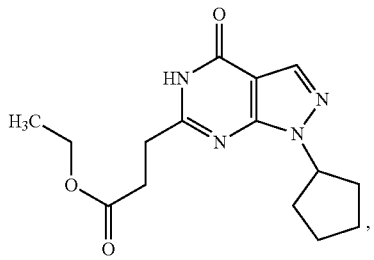
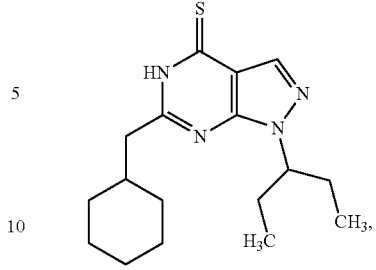
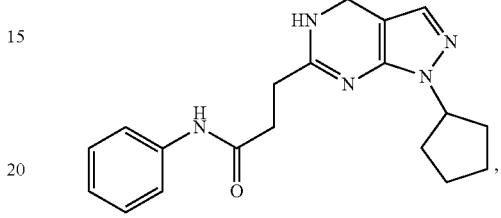
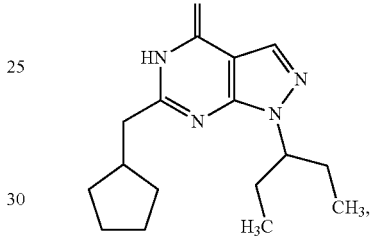
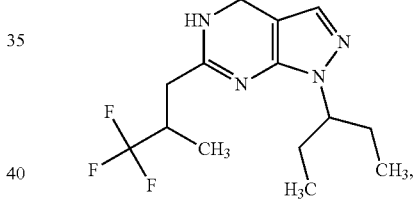
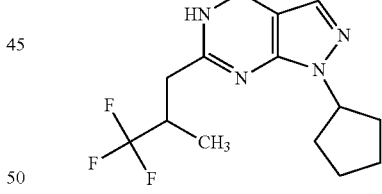
or the salts thereof.
* * * * *